(12) United States Patent
Balakin

(10) Patent No.: US 8,089,054 B2
(45) Date of Patent: Jan. 3, 2012

(54) CHARGED PARTICLE BEAM ACCELERATION AND EXTRACTION METHOD AND APPARATUS USED IN CONJUNCTION WITH A CHARGED PARTICLE CANCER THERAPY SYSTEM

(76) Inventor: Vladimir Balakin, Protvino (RU)

( * ) Notice: Subject to any disclaimer, the term of this patent is extended or adjusted under 35 U.S.C. 154(b) by 415 days.

(21) Appl. No.: 12/499,669

(22) Filed: Jul. 8, 2009

(65) Prior Publication Data

US 2009/0309040 A1 Dec. 17, 2009

Related U.S. Application Data

(63) Continuation-in-part of application No. 12/425,683, filed on Apr. 17, 2009, now Pat. No. 7,939,809.

(60) Provisional application No. 61/055,395, filed on May 22, 2008, provisional application No. 61/137,574, filed on Aug. 1, 2008, provisional application No. 61/192,245, filed on Sep. 17, 2008, provisional application No. 61/055,409, filed on May 22, 2008, provisional application No. 61/203,308, filed on Dec. 22, 2008, provisional application No. 61/188,407, filed on Aug. 11, 2008, provisional application No. 61/188,406, filed on Aug. 11, 2008, provisional application No. 61/189,815, filed on Aug. 25, 2008, provisional application No. 61/201,731, filed on Dec. 15, 2008, provisional application No. 61/205,362, filed on Jan. 21, 2009, provisional application No. 61/134,717, filed on Jul. 14, 2008, provisional application No. 61/134,707, filed on Jul. 14, 2008, provisional application No. 61/201,732, filed on Dec. 15, 2008, provisional application No. 61/198,509, filed on Nov. 7, 2008, provisional application No. 61/134,718, filed on Jul. 14, 2008, provisional application No. 61/190,613, filed on Sep. 2, 2008, provisional application No. 61/191,043, filed on Sep. 8, 2008, provisional application No. 61/192,237, filed on Sep. 17, 2008, provisional application No. 61/201,728, filed on Dec. 15, 2008, provisional application No. 61/190,546, filed on Sep. 2, 2008, provisional application No. 61/189,017, filed on Aug. 15, 2008, provisional application No. 61/198,248, filed on Nov. 5, 2008, provisional application No. 61/198,508, filed on Nov. 7, 2008, provisional application No. 61/197,971, filed on Nov. 3, 2008, provisional application No. 61/199,405, filed on Nov. 17, 2008, provisional application No. 61/199,403, filed on Nov. 17, 2008, provisional application No. 61/199,404, filed on Nov. 17, 2008, provisional application No. 61/209,529, filed on Mar. 9, 2009, provisional application No. 61/208,182, filed on Feb. 23, 2009, provisional application No. 61/208,971, filed on Mar. 3, 2009.

(51) Int. Cl.
*A61N 5/00* (2006.01)

(52) U.S. Cl. .............. 250/492.1; 250/396 R; 250/492.3; 313/62; 315/503; 315/504

(58) Field of Classification Search .............. 250/396 R, 250/492.1, 492.3; 313/62; 315/503, 504
See application file for complete search history.

(56) References Cited

U.S. PATENT DOCUMENTS

| | | |
|---|---|---|
| 2,306,875 A | 12/1942 | Fremlin |
| 2,790,902 A | 4/1957 | Wright |
| 3,128,405 A | 4/1964 | Lambertson |
| 3,412,337 A | 11/1968 | Lothrop |
| 3,655,968 A | 4/1972 | Moore |
| 3,867,705 A | 2/1975 | Hudson |
| 3,882,339 A | 5/1975 | Rate |
| 3,906,280 A | 9/1975 | Andelfinger |
| 4,344,011 A | 8/1982 | Hayashi |
| 4,607,380 A | 8/1986 | Oliver |
| 4,622,687 A | 11/1986 | Whitaker |
| 4,726,046 A | 2/1988 | Nunan |
| 4,730,353 A | 3/1988 | Ono |
| 4,868,844 A | 9/1989 | Nunan |
| 4,870,287 A * | 9/1989 | Cole et al. .................. 250/492.3 |
| 5,017,789 A | 5/1991 | Young |
| 5,039,867 A | 8/1991 | Nishihara |
| 5,073,913 A | 12/1991 | Martin |

| Patent No. | Date | Inventor |
|---|---|---|
| 5,168,241 A | 12/1992 | Hirota |
| 5,177,448 A | 1/1993 | Ikeguchi |
| 5,260,581 A | 11/1993 | Lesyna |
| 5,285,166 A | 2/1994 | Hiramoto |
| 5,349,198 A | 9/1994 | Takanaka |
| 5,363,008 A | 11/1994 | Hiramoto |
| 5,388,580 A | 2/1995 | Sullivan |
| 5,440,133 A | 8/1995 | Moyers |
| 5,483,129 A | 1/1996 | Yamamoto |
| 5,511,549 A | 4/1996 | Legg |
| 5,538,494 A | 7/1996 | Matsuda |
| 5,576,549 A | 11/1996 | Hell |
| 5,585,642 A | 12/1996 | Britton |
| 5,600,213 A | 2/1997 | Hiramoto |
| 5,626,682 A | 5/1997 | Kobari |
| 5,633,907 A | 5/1997 | Gravelle |
| 5,659,223 A | 8/1997 | Goodman |
| 5,661,366 A | 8/1997 | Hirota |
| 5,668,371 A | 9/1997 | Deasy |
| 5,698,954 A | 12/1997 | Hirota |
| 5,760,395 A | 6/1998 | Johnstone |
| 5,789,875 A | 8/1998 | Hiramoto |
| 5,818,058 A | 10/1998 | Nakanishi |
| 5,820,320 A | 10/1998 | Kobari |
| 5,825,845 A | 10/1998 | Blair |
| 5,866,912 A | 2/1999 | Slater |
| 5,895,926 A | 4/1999 | Britton |
| 5,907,595 A | 5/1999 | Sommerer |
| 5,917,293 A | 6/1999 | Saito |
| 5,969,367 A | 10/1999 | Hiramoto |
| 5,986,274 A | 11/1999 | Akiyama |
| 5,993,373 A | 11/1999 | Nonaka |
| 6,008,499 A | 12/1999 | Hiramoto |
| 6,034,377 A | 3/2000 | Pu |
| 6,087,670 A | 7/2000 | Hiramoto |
| 6,087,672 A | 7/2000 | Matsuda |
| 6,148,058 A | 11/2000 | Dobbs |
| 6,207,952 B1 | 3/2001 | Kan |
| 6,218,675 B1 | 4/2001 | Akiyama |
| 6,236,043 B1 | 5/2001 | Tadokoro |
| 6,265,837 B1 | 7/2001 | Akiyama |
| 6,282,263 B1 | 8/2001 | Arndt |
| 6,316,776 B1 | 11/2001 | Hiramoto |
| 6,322,249 B1 | 11/2001 | Wofford |
| 6,335,535 B1 | 1/2002 | Miyake |
| 6,339,635 B1 | 1/2002 | Schardt |
| 6,356,617 B1 | 3/2002 | Besch |
| 6,365,894 B2 | 4/2002 | Tadokoro |
| 6,421,416 B1 | 7/2002 | Sliski |
| 6,433,349 B2 | 8/2002 | Akiyama |
| 6,433,494 B1 | 8/2002 | Kulish |
| 6,437,513 B1 | 8/2002 | Stelzer |
| 6,444,990 B1 | 9/2002 | Morgan |
| 6,462,490 B1 | 10/2002 | Matsuda |
| 6,470,068 B2 | 10/2002 | Cheng |
| 6,472,834 B2 | 10/2002 | Hiramoto |
| 6,476,403 B1 | 11/2002 | Dolinskii |
| 6,545,436 B1 | 4/2003 | Gary |
| 6,560,354 B1 | 5/2003 | Maurer, Jr. |
| 6,580,084 B1 | 6/2003 | Hiramoto |
| 6,597,005 B1 | 7/2003 | Badura |
| 6,600,164 B1 | 7/2003 | Badura |
| 6,614,038 B1 | 9/2003 | Brand |
| 6,617,598 B1 | 9/2003 | Matsuda |
| 6,626,842 B2 | 9/2003 | Oka |
| 6,635,882 B1 | 10/2003 | Pavlovic |
| 6,639,234 B1 | 10/2003 | Badura |
| 6,670,618 B1 | 12/2003 | Hartmann |
| 6,683,318 B1 | 1/2004 | Haberer |
| 6,710,362 B2 | 3/2004 | Kraft |
| 6,717,162 B1 | 4/2004 | Jongen |
| 6,730,921 B2 | 5/2004 | Kraft |
| 6,736,831 B1 | 5/2004 | Hartmann |
| 6,745,072 B1 | 6/2004 | Badura |
| 6,774,383 B2 | 8/2004 | Norimine |
| 6,777,700 B2 | 8/2004 | Yanagisawa |
| 6,785,359 B2 | 8/2004 | Lemaitre |
| 6,787,771 B2 | 9/2004 | Bashkirov |
| 6,792,078 B2 | 9/2004 | Kato |
| 6,799,068 B1 | 9/2004 | Hartmann |
| 6,800,866 B2 | 10/2004 | Amemiya |
| 6,803,591 B2 | 10/2004 | Muramatsu |
| 6,809,325 B2 | 10/2004 | Dahl |
| 6,819,743 B2 | 11/2004 | Kato |
| 6,822,244 B2 | 11/2004 | Beloussov |
| 6,823,045 B2 | 11/2004 | Kato |
| 6,838,676 B1 | 1/2005 | Jackson |
| 6,859,741 B2 | 2/2005 | Haberer |
| 6,881,970 B2 | 4/2005 | Akiyama |
| 6,891,177 B1 | 5/2005 | Kraft |
| 6,897,451 B2 | 5/2005 | Kaercher |
| 6,900,446 B2 | 5/2005 | Akiyama |
| 6,903,351 B1 | 6/2005 | Akiyama |
| 6,903,356 B2 | 6/2005 | Muramatsu |
| 6,931,100 B2 | 8/2005 | Kato |
| 6,936,832 B2 | 8/2005 | Norimine |
| 6,937,696 B1 | 8/2005 | Mostafavi |
| 6,953,943 B2 | 10/2005 | Yanagisawa |
| 6,979,832 B2 | 12/2005 | Yanagisawa |
| 6,984,835 B2 | 1/2006 | Harada |
| 6,992,312 B2 | 1/2006 | Yanagisawa |
| 7,012,267 B2 | 3/2006 | Moriyama |
| 7,026,636 B2 | 4/2006 | Yanagisawa |
| 7,030,396 B2 | 4/2006 | Muramatsu |
| 7,045,781 B2 | 5/2006 | Adamec |
| 7,049,613 B2 | 5/2006 | Yanagisawa |
| 7,053,389 B2 | 5/2006 | Yanagisawa |
| 7,054,801 B2 | 5/2006 | Sakamoto |
| 7,058,158 B2 | 6/2006 | Sako |
| 7,060,997 B2 | 6/2006 | Norimine |
| 7,071,479 B2 | 7/2006 | Yanagisawa |
| 7,081,619 B2 | 7/2006 | Bashkirov |
| 7,084,410 B2 | 8/2006 | Beloussov |
| 7,091,478 B2 | 8/2006 | Haberer |
| 7,102,144 B2 | 9/2006 | Matsuda |
| 7,109,505 B1 | 9/2006 | Sliski |
| 7,122,811 B2 | 10/2006 | Matsuda |
| 7,141,810 B2 | 11/2006 | Kakiuchi |
| 7,154,107 B2 | 12/2006 | Yanagisawa |
| 7,154,108 B2 | 12/2006 | Tadokoro |
| 7,173,264 B2 | 2/2007 | Moriyama |
| 7,173,265 B2 | 2/2007 | Miller |
| 7,193,227 B2 | 3/2007 | Hiramoto |
| 7,199,382 B2 | 4/2007 | Rigney |
| 7,208,748 B2 | 4/2007 | Sliski |
| 7,212,608 B2 | 5/2007 | Nagamine |
| 7,212,609 B2 | 5/2007 | Nagamine |
| 7,227,161 B2 | 6/2007 | Matsuda |
| 7,247,869 B2 | 7/2007 | Tadokoro |
| 7,259,529 B2 | 8/2007 | Tanaka |
| 7,262,424 B2 | 8/2007 | Moriyama |
| 7,274,018 B2 | 9/2007 | Adamec |
| 7,274,025 B2 | 9/2007 | Berdermann |
| 7,280,633 B2 | 10/2007 | Cheng |
| 7,297,967 B2 | 11/2007 | Yanagisawa |
| 7,301,162 B2 | 11/2007 | Matsuda |
| 7,310,404 B2 | 12/2007 | Tashiro |
| 7,315,606 B2 | 1/2008 | Tsujii |
| 7,319,231 B2 | 1/2008 | Moriyama |
| 7,345,292 B2 | 3/2008 | Moriyama |
| 7,351,988 B2 | 4/2008 | Naumann |
| 7,355,189 B2 | 4/2008 | Yanagisawa |
| 7,356,112 B2 | 4/2008 | Brown |
| 7,368,740 B2 | 5/2008 | Beloussov |
| 7,372,053 B2 | 5/2008 | Yamashita |
| 7,381,979 B2 | 6/2008 | Yamashita |
| 7,432,516 B2 * | 10/2008 | Peggs et al. ............... 250/492.3 |
| 7,634,057 B2 | 12/2009 | Ein-Gal |
| 7,668,585 B2 | 2/2010 | Green |
| 7,729,469 B2 | 6/2010 | Kobayashi |
| 7,741,623 B2 | 6/2010 | Sommer |
| 7,796,730 B2 | 9/2010 | Marash |
| 7,801,277 B2 | 9/2010 | Zou |
| 2003/0163015 A1 | 8/2003 | Yanagisawa |
| 2003/0164459 A1 | 9/2003 | Schardt |
| 2004/0022361 A1 | 2/2004 | Lemaitre |
| 2005/0211905 A1 | 9/2005 | Stark |
| 2007/0093723 A1 | 4/2007 | Keall |

| | | |
|---|---|---|
| 2007/0170994 A1 | 7/2007 | Pegss |
| 2008/0191142 A1 | 8/2008 | Pedroni |
| 2010/0008468 A1 | 1/2010 | Balakin |
| 2010/0008469 A1 | 1/2010 | Balakin |
| 2010/0128846 A1 | 5/2010 | Balakin |

FOREIGN PATENT DOCUMENTS

| | | |
|---|---|---|
| EP | 1683545 A2 | 7/2006 |
| WO | WO 2008/044194 A2 | 4/2008 |

OTHER PUBLICATIONS

Adams, "Electrostatic cylinder lenses II: Three Element Einzel Lenses", Journal, Feb. 1, 1972, pp. 150-155, XP002554355, vol. 5 No. 2, Journal of Physics E.

Amaldi, "A Hospital-Based Hadrontherapy Complex", Journal, Jun. 27, 1994, pp. 49-51, XP002552288, Proceedings of Epac 94, London, England.

Arimoto, "A Study of the PRISM-FFAG Magnet", Journal, Oct. 18, 2004,Oct. 22, 2004, pp. 243-245, XP002551810, Proceedings of Cyclotron 2004 Conference, Tokyo, Japan.

Biophysics Group, "Design Construction and First Experiments of a Magnetic Scanning System for Therapy. Radiobiological Experiment on the Radiobiological Action of Carbon, Oxygen and Neon", Book, Jun. 1, 1991, pp. 1-31, XP009121701, vol. GSI-91-18, GSI Report, Darmstadt ,DE.

Blackmore, "Operation of the TRIUMF Proton Therapy Facility", Book, May 12, 1997, pp. 3831-3833, XP010322373, vol. 3, Proceedings of the 1997 Particle Accelerator Conference, NJ, USA.

Bryant, "Proton-Ion Medical Machine Study (PIMMS) Part II", Book, Jul. 27, 2000, p. 23,p. 228,pp. 289-290, XP002551811, European Organisation for Nuclear Research Cern-Ps Division, Geneva, Switzerland.

Craddock, "New Concepts in FFAG Design for Secondary Beam Facilities and other Applications", Journal, May 15, 2005,May 20, 2005, pp. 261-265, XP002551806, Proceedings of 2005 Particle Accelerator Conference, Knoxville, Tennessee, USA.

Dzhelepov, "Use of USSR Proton Accelerators for Medical Purposes", Journal,Jun. 1973, pp. 268-270, vol. ns-2- No. 3, XP002553045, IEEE Transactions on Nuclear Science USA, USA.

Endo, "Medical Synchrotron for Proton Therapy" Journal, Jun. 7, 1988,Jun. 11, 1988, pp. 1459-1461, XP002551808, Proceedings of Epac 88, Rome, Italy.

Johnstone, Koscielniak, "Tune-Stabilized Linear-Field FFAG for Carbon Therapy", Journal, Jun. 26, 2006,Jun. 30, 2006, XP002551807, Proceedings of Epac 2006, Edinburgh, Scotland, UK.

Kalnins, "The use of electric multipole lenses for bending and focusing polar molecules, with application to the design of a rotational-state separator", Journal, May 17, 2003,May 21, 2003, pp. 2951-2953, XP002554356, Proceeding of Pac 2003, Portland, Oregon, USA.

Kim, "50 MeV Proton Beam Test Facility for Low Flux Beam Utilization Studies of PEFP", Journal, Oct. 31, 2005, pp. 441-443, XP002568008, Proceedings of Apac 2004, Pohang, Korea.

Lapostolle, "Introduction a la theorie des accelerateurs lineaires", Book, Jul. 10, 1987, pp. 4-5, XP002554354, Cern Yellow Book Cern, Geneva, Switzerland.

Li, "A thin Beryllium Injection Window for CESR-C", Book, May 12, 2003, pp. 2264-2266, XP002568010, vol. 4, PAC03, Portland, Oregon, USA.

Noda, "Slow beam extraction by a transverse RF field with AM and FM", Journal, May 21, 1996, pp. 269-277, vol. A374, XP002552289, Nuclear Instruments and Methods in Physics Research A, Eslevier, Amsterdam, NL.

Noda, "Performance of a respiration-gated beam control system for patient treatment", Journal, Jun. 10, 1996,Jun. 14, 1996, pp. 2656-2658, XP002552290, Proceedings Epac 96, Barcelona, Spain.

Peters, "Negative ion sources for high energy accelerators", Journal, Feb. 1, 2002, pp. 1069-1074, XP012037926, vol. 71—No. 2,Review of Scientific Instruments, Melville, NY, USA.

Pohlit, "Optimization of Cancer Treatment with Accelerator Produced Radiations", Journal, Jun. 22, 1998, pp. 192-194, XP002552855, Proceedings EPAC 98, Stockholm, Sweden.

Saito, "RF Accelerating System for Compact Ion Synchrotron", Journal, Jun. 18, 2001, pp. 966-968, XP002568009, Proceeding of 2001 Pac, Chicago, USA.

Suda, "Medical Application of the Positron Emitter Beam at HIMAC", Journal, Jun. 26, 2000, Jun. 30, 2000, pp. 2554-2556, XP002553046, Proceedings of EPAC 2000, Vienna, Austria.

Tanigaki, "Construction of FFAG Accelerators in KURRI for ADS Study", May 16, 2005,May 20, 2005, pp. 350-352, XP002551809, Proceedings of 2005 Particle Accelerator Conference, Knoxville, Tennessee, USA.

Trbojevic, "Design of a Non-Scaling FFAG Accelerator for Proton Therapy", Journal, Oct. 18, 2004,Oct. 22, 2004, pp. 246-248, XP002551805, Proceedings of 2004 Cyclotron Conference, Tokyo, Japan.

Winkler, "Charge Exchange Extraction at the Experimental Storage Ring ESR at GSI", Journal, Jun. 22, 1998, p. 559-561, XP002552287, Proceedings of Epac 98, Stockholm, Sweden.

\* cited by examiner

*Primary Examiner* — Michael Maskell

(74) *Attorney, Agent, or Firm* — Kevin H. Hazen

(57) ABSTRACT

The invention comprises a charged particle beam acceleration and/or extraction method and apparatus used in conjunction with charged particle beam radiation therapy of cancerous tumors. Novel design features of a synchrotron are described. Particularly, turning magnets, edge focusing magnets, and extraction elements are described that minimize the overall size of the synchrotron, provide a tightly controlled proton beam, directly reduce the size of required magnetic fields, directly reduces required operating power, and allow continual acceleration of protons in a synchrotron even during a process of extracting protons from the synchrotron.

21 Claims, 7 Drawing Sheets

CHARGED PARTICLE BEAM ACCELERATION AND EXTRACTION METHOD AND APPARATUS USED IN CONJUNCTION WITH A CHARGED PARTICLE CANCER THERAPY SYSTEM

CROSS REFERENCES TO RELATED APPLICATIONS

This application:
is a continuation-in-part of U.S. patent application Ser. No. 12/425,683 filed Apr. 17, 2009 now U.S. Pat. No. 7,939,809, which claims the benefit of:
  U.S. provisional patent application No. 61/055,395 filed May 22, 2008;
  U.S. provisional patent application No. 61/137,574 filed Aug. 1, 2008;
  U.S. provisional patent application No. 61/192,245 filed Sep. 17, 2008;
  U.S. provisional patent application No. 61/055,409 filed May 22, 2008;
  U.S. provisional patent application No. 61/203,308 filed Dec. 22, 2008;
  U.S. provisional patent application No. 61/188,407 filed Aug. 11, 2008;
  U.S. provisional patent application No. 61/188,406 filed Aug. 11, 2008;
  U.S. provisional patent application No. 61/189,815 filed Aug. 25, 2008;
  U.S. provisional patent application No. 61/201,731 filed Dec. 15, 2008;
  U.S. provisional patent application No. 61/205,362 filed Jan. 12, 2009;
  U.S. provisional patent application No. 61/134,717 filed Jul. 14, 2008;
  U.S. provisional patent application No. 61/134,707 filed Jul. 14, 2008;
  U.S. provisional patent application No. 61/201,732 filed Dec. 15, 2008;
  U.S. provisional patent application No. 61/198,509 filed Nov. 7, 2008;
  U.S. provisional patent application No. 61/134,718 filed Jul. 14, 2008;
  U.S. provisional patent application No. 61/190,613 filed Sep. 2, 2008;
  U.S. provisional patent application No. 61/191,043 filed Sep. 8, 2008;
  U.S. provisional patent application No. 61/192,237 filed Sep. 17, 2008;
  U.S. provisional patent application No. 61/201,728 filed Dec. 15, 2008;
  U.S. provisional patent application No. 61/190,546 filed Sep. 2, 2008;
  U.S. provisional patent application No. 61/189,017 filed Aug. 15, 2008;
  U.S. provisional patent application No. 61/198,248 filed Nov. 5, 2008;
  U.S. provisional patent application No. 61/198,508 filed Nov. 7, 2008;
  U.S. provisional patent application No. 61/197,971 filed Nov. 3, 2008;
  U.S. provisional patent application No. 61/199,405 filed Nov. 17, 2008;
  U.S. provisional patent application No. 61/199,403 filed Nov. 17, 2008; and
  U.S. provisional patent application No. 61/199,404 filed Nov. 17, 2008;
claims the benefit of U.S. provisional patent application No. 61/209,529 filed Mar. 9, 2009;
claims the benefit of U.S. provisional patent application No. 61/208,182 filed Feb. 23, 2009;
claims the benefit of U.S. provisional patent application No. 61/208,971 filed Mar. 3, 2009; and
claims priority to PCT patent application serial No.: PCT/RU2009/00015, filed Mar. 4, 2009,
all of which are incorporated herein in their entirety by this reference thereto.

BACKGROUND OF THE INVENTION

1. Field of the Invention

This invention relates generally to treatment of solid cancers. More particularly, the invention relates to a charged particle beam acceleration and extraction method and apparatus used in conjunction with radiation treatment of cancerous tumors.

2. Discussion of the Prior Art

Cancer

A tumor is an abnormal mass of tissue. Tumors are either benign or malignant. A benign tumor grows locally, but does not spread to other parts of the body. Benign tumors cause problems because of their spread, as they press and displace normal tissues. Benign tumors are dangerous in confined places such as the skull. A malignant tumor is capable of invading other regions of the body. Metastasis is cancer spreading by invading normal tissue and spreading to distant tissues.

Cancer Treatment

Several forms of radiation therapy exist for cancer treatment including: brachytherapy, traditional electromagnetic X-ray therapy, and proton therapy. Each are further described, infra.

Brachytherapy is radiation therapy using radioactive sources implanted inside the body. In this treatment, an oncologist implants radioactive material directly into the tumor or very close to it. Radioactive sources are also placed within body cavities, such as the uterine cervix.

The second form of traditional cancer treatment using electromagnetic radiation includes treatment using X-rays and gamma rays. An X-ray is high-energy, ionizing, electromagnetic radiation that is used at low doses to diagnose disease or at high doses to treat cancer. An X-ray or Röntgen ray is a form of electromagnetic radiation with a wavelength in the range of 10 to 0.01 nanometers (nm), corresponding to frequencies in the range of 30 PHz to 30 EHz. X-rays are longer than gamma rays and shorter than ultraviolet rays. X-rays are primarily used for diagnostic radiography. X-rays are a form of ionizing radiation and as such can be dangerous. Gamma rays are also a form of electromagnetic radiation and are at frequencies produced by sub-atomic particle interactions, such as electron-positron annihilation or radioactive decay. In the electromagnetic spectrum, gamma rays are generally characterized as electromagnetic radiation having the highest frequency, as having highest energy, and having the shortest wavelength, such as below about 10 picometers. Gamma rays consist of high energy photons with energies above about 100 keV. X-rays are commonly used to treat cancerous tumors. However, X-rays are not optimal for treatment of cancerous tissue as X-rays deposit their highest does of radiation near the surface of the targeted tissue and delivery exponentially less radiation as they penetrate into the tissue. This results in large amounts of radiation being delivered outside of the tumor. Gamma rays have similar limitations.

The third form of cancer treatment uses protons. Proton therapy systems typically include: a beam generator, an accelerator, and a beam transport system to move the resulting accelerated protons to a plurality of treatment rooms where the protons are delivered to a tumor in a patient's body.

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Due to their relatively enormous size, protons scatter less easily in the tissue and there is very little lateral dispersion. Hence, the proton beam stays focused on the tumor shape without much lateral damage to surrounding tissue. All protons of a given energy have a certain range, defined by the Bragg peak, and the dosage delivery to tissue ratio is maximum over just the last few millimeters of the particle's range. The penetration depth depends on the energy of the particles, which is directly related to the speed to which the particles were accelerated by the proton accelerator. The speed of the proton is adjustable to the maximum rating of the accelerator. It is therefore possible to focus the cell damage due to the proton beam at the very depth in the tissues where the tumor is situated. Tissues situated before the Bragg peak receive some reduced dose and tissues situated after the peak receive none.

Synchrotrons

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Injection

K. Hiramoto, et. al. "Accelerator System", U.S. Pat. No. 4,870,287 (Sep. 26, 1989) describes an accelerator system having a selector electromagnet for introducing an ion beam accelerated by pre-accelerators into either a radioisotope producing unit or a synchrotron.

K. Hiramoto, et. al. "Circular Accelerator, Method of Injection of Charged Particle Thereof, and Apparatus for Injection of Charged Particle Thereof", U.S. Pat. No. 5,789,875 (Aug. 4, 1998) and K. Hiramoto, et. al. "Circular Accelerator, Method of Injection of Charged Particle Thereof, and Apparatus for Injection of Charged Particle Thereof", U.S. Pat. No. 5,600,213 (Feb. 4, 1997) both describe a method and apparatus for injecting a large number of charged particles into a vacuum duct where the beam of injection has a height and width relative to a geometrical center of the duct.

Accelerator/Synchrotron

H. Tanaka, et. al. "Charged Particle Accelerator", U.S. Pat. No. 7,259,529 (Aug. 21, 2007) describe a charged particle accelerator having a two period acceleration process with a fixed magnetic field applied in the first period and a timed second acceleration period to provide compact and high power acceleration of the charged particles.

T. Haberer, et. al. "Ion Beam Therapy System and a Method for Operating the System", U.S. Pat. No. 6,683,318 (Jan. 27, 2004) describe an ion beam therapy system and method for operating the system. The ion beam system uses a gantry that has vertical deflection system and a horizontal deflection system positioned before a last bending magnet that result in a parallel scanning mode resulting from an edge focusing effect.

V. Kulish, et. al. "Inductional Undulative EH-Accelerator", U.S. Pat. No. 6,433,494 (Aug. 13, 2002) describe an inductive undulative EH-accelerator for acceleration of beams of charged particles. The device consists of an electromagnet undulation system, whose driving system for electromagnets is made in the form of a radio-frequency (RF) oscillator operating in the frequency range from about 100 KHz to 10 GHz.

K. Saito, et. al. "Radio-Frequency Accelerating System and Ring Type Accelerator Provided with the Same", U.S. Pat. No. 5,917,293 (Jun. 29, 1999) describe a radio-frequency accelerating system having a loop antenna coupled to a magnetic core group and impedance adjusting means connected to the loop antenna. A relatively low voltage is applied to the impedance adjusting means allowing small construction of the adjusting means.

J. Hirota, et. al. "Ion Beam Accelerating Device Having Separately Excited Magnetic Cores", U.S. Pat. No. 5,661,366 (Aug. 26, 1997) describe an ion beam accelerating device having a plurality of high frequency magnetic field inducing units and magnetic cores.

J. Hirota, et. al. "Acceleration Device for Charged Particles", U.S. Pat. No. 5,168,241 (Dec. 1, 1992) describe an acceleration cavity having a high frequency power source and a looped conductor operating under a control that combine to control a coupling constant and/or de-tuning allowing transmission of power more efficiently to the particles.

Vacuum Chamber

T. Kobari, et. al. "Apparatus For Treating the Inner Surface of Vacuum Chamber", U.S. Pat. No. 5,820,320 (Oct. 13, 1998) and T. Kobari, et. al. "Process and Apparatus for Treating Inner Surface Treatment of Chamber and Vacuum Chamber", U.S. Pat. No. 5,626,682 (May 6, 1997) both describe an apparatus for treating an inner surface of a vacuum chamber including means for supplying an inert gas or nitrogen to a surface of the vacuum chamber with a broach. Alternatively, the broach is used for supplying a lower alcohol to the vacuum chamber for dissolving contaminants on the surface of the vacuum chamber.

Magnet Shape

M. Tadokoro, et. al. "Electromagnetic and Magnetic Field Generating Apparatus", U.S. Pat. No. 6,365,894 (Apr. 2, 2002) and M. Tadokoro, et. al. "Electromagnetic and Magnetic Field Generating Apparatus", U.S. Pat. No. 6,236,043 (May 22, 2001) each describe a pair of magnetic poles, a return yoke, and exciting coils. The interior of the magnetic poles each have a plurality of air gap spacers to increase magnetic field strength.

Extraction

T. Nakanishi, et. al. "Charged-Particle Beam Accelerator, Particle Beam Radiation Therapy System Using the Charged-Particle Beam Accelerator, and Method of Operating the Particle Beam Radiation Therapy System", U.S. Pat. No. 7,122,978 (Oct. 17, 2006) describe a charged particle beam accelerator having an RF-KO unit for increasing amplitude of betatron oscillation of a charged particle beam within a stable region of resonance and an extraction quadrupole electromagnet unit for varying a stable region of resonance. The RF-KO unit is operated within a frequency range in which the circulating beam does not go beyond a boundary of stable region of resonance and the extraction quadrupole electromagnet is operated with timing required for beam extraction.

T. Haberer, et. al. "Method and Device for Controlling a Beam Extraction Raster Scan Irradiation Device for Heavy Ions or Protons", U.S. Pat. No. 7,091,478 (Aug. 15, 2006) describe a method for controlling beam extraction irradiation in terms of beam energy, beam focusing, and beam intensity for every accelerator cycle.

K. Hiramoto, et. al. "Accelerator and Medical System and Operating Method of the Same", U.S. Pat. No. 6,472,834 (Oct. 29, 2002) describe a cyclic type accelerator having a deflection electromagnet and four-pole electromagnets for making a charged particle beam circulate, a multi-pole electromagnet for generating a stability limit of resonance of betatron oscillation, and a high frequency source for applying a high frequency electromagnetic field to the beam to move the beam to the outside of the stability limit. The high frequency source generates a sum signal of a plurality of alternating current (AC) signals of which the instantaneous frequencies change with respect to time, and of which the average values of the instantaneous frequencies with respect to time are different. The system applies the sum signal via electrodes to the beam.

K. Hiramoto, et. al. "Synchrotron Type Accelerator and Medical Treatment System Employing the Same", U.S. Pat. No. 6,087,670 (Jul. 11, 2000) and K. Hiramoto, et. al. "Synchrotron Type Accelerator and Medical Treatment System Employing the Same", U.S. Pat. No. 6,008,499 (Dec. 28, 1999) describe a synchrotron accelerator having a high frequency applying unit arranged on a circulating orbit for applying a high frequency electromagnetic field to a charged particle beam circulating and for increasing amplitude of betatron oscillation of the particle beam to a level above a stability limit of resonance. Additionally, for beam ejection, four-pole divergence electromagnets are arranged: (1) downstream with respect to a first deflector; (2) upstream with respect to a deflecting electromagnet; (3) downstream with respect to the deflecting electromagnet; and (4) and upstream with respect to a second deflector.

K. Hiramoto, et. al. "Circular Accelerator and Method and Apparatus for Extracting Charged-Particle Beam in Circular Accelerator", U.S. Pat. No. 5,363,008 (Nov. 8, 1994) describe a circular accelerator for extracting a charged-particle beam that is arranged to: (1) increase displacement of a beam by the effect of betatron oscillation resonance; (2) to increase the betatron oscillation amplitude of the particles, which have an initial betatron oscillation within a stability limit for resonance; and (3) to exceed the resonance stability limit thereby extracting the particles exceeding the stability limit of the resonance.

K. Hiramoto, et. al. "Method of Extracting Charged Particles from Accelerator, and Accelerator Capable Carrying Out the Method, by Shifting Particle Orbit", U.S. Pat. No. 5,285,166 (Feb. 8, 1994) describe a method of extracting a charged particle beam. An equilibrium orbit of charged particles maintained by a bending magnet and magnets having multipole components greater than sextuple components is shifted by a constituent element of the accelerator other than these magnets to change the tune of the charged particles.

Transport/Scanning Control

K. Matsuda, et. al. "Particle Beam Irradiation Apparatus, Treatment Planning Unit, and Particle Beam Irradiation Method", U.S. Pat. No. 7,227,161 (Jun. 5, 2007); K. Matsuda, et. al. "Particle Beam Irradiation Treatment Planning Unit, and Particle Beam Irradiation Method", U.S. Pat. No. 7,122,811 (Oct. 17, 2006); and K. Matsuda, et. al. "Particle Beam Irradiation Apparatus, Treatment Planning Unit, and Particle Beam Irradiation Method" (Sep. 5, 2006) describe a particle beam irradiation apparatus have a scanning controller that stops output of an ion beam, changes irradiation position via control of scanning electromagnets, and reinitiates treatment based on treatment planning information.

T. Norimine, et. al. "Particle Therapy System Apparatus", U.S. Pat. No. 7,060,997 (Jun. 13, 2006); T. Norimine, et. al. "Particle Therapy System Apparatus", U.S. Pat. No. 6,936,832 (Aug. 30, 2005); and T. Norimine, et. al. "Particle Therapy System Apparatus", U.S. Pat. No. 6,774,383 (Aug. 10, 2004) each describe a particle therapy system having a first steering magnet and a second steering magnet disposed in a charged particle beam path after a synchrotron that are controlled by first and second beam position monitors.

K. Moriyama, et. al. "Particle Beam Therapy System", U.S. Pat. No. 7,012,267 (Mar. 14, 2006) describe a manual input to a ready signal indicating preparations are completed for transport of the ion beam to a patient.

H. Harada, et. al. "Irradiation Apparatus and Irradiation Method", U.S. Pat. No. 6,984,835 (Jan. 10, 2006) describe an irradiation method having a large irradiation filed capable of uniform dose distribution, without strengthening performance of an irradiation field device, using a position controller having overlapping area formed by a plurality of irradiations using a multileaf collimator. The system provides flat and uniform dose distribution over an entire surface of a target.

H. Akiyama, et. al. "Charged Particle Beam Irradiation Equipment Having Scanning Electromagnet Power Supplies", U.S. Pat. No. 6,903,351 (Jun. 7, 2005); H. Akiyama, et. al. "Charged Particle Beam Irradiation Equipment Having Scanning Electromagnet Power Supplies", U.S. Pat. No. 6,900,436 (May 31, 2005); and H. Akiyama, et. al. "Charged Particle Beam Irradiation Equipment Having Scanning Electromagnet Power Supplies", U.S. Pat. No. 6,881,970 (Apr. 19, 2005) all describe a power supply for applying a voltage to a scanning electromagnet for deflecting a charged particle beam and a second power supply without a pulsating component to control the scanning electromagnet more precisely allowing for uniform irradiation of the irradiation object.

K. Amemiya, et. al. "Accelerator System and Medical Accelerator Facility", U.S. Pat. No. 6,800,866 (Oct. 5, 2004) describe an accelerator system having a wide ion beam control current range capable of operating with low power consumption and having a long maintenance interval.

A. Dolinskii, et. al. "Gantry with an Ion-Optical System", U.S. Pat. No. 6,476,403 (Nov. 5, 2002) describe a gantry for an ion-optical system comprising an ion source and three bending magnets for deflecting an ion beam about an axis of rotation. A plurality of quadrupoles are also provided along the beam path to create a fully achromatic beam transport and an ion beam with difference emittances in the horizontal and vertical planes. Further, two scanning magnets are provided between the second and third bending magnets to direct the beam.

H. Akiyama, et. al. "Charged Particle Beam Irradiation Apparatus", U.S. Pat. No. 6,218,675 (Apr. 17, 2001) describe a charged particle beam irradiation apparatus for irradiating a target with a charged particle beam that include a plurality of scanning electromagnets and a quadrupole electromagnet between two of the plurality of scanning electromagnets.

K. Matsuda, et. al. "Charged Particle Beam Irradiation System and Method Thereof", U.S. Pat. No. 6,087,672 (Jul. 11, 2000) describe a charged particle beam irradiation system having a ridge filter with shielding elements to shield a part of the charged particle beam in an area corresponding to a thin region in said target.

P. Young, et. al. "Raster Scan Control System for a Charged-Particle Beam", U.S. Pat. No. 5,017,789 (May 21, 1991) describe a raster scan control system for use with a charged-particle beam delivery system that includes a nozzle through which a charged particle beam passes. The nozzle includes a programmable raster generator and both fast and slow sweep scan electromagnets that cooperate to generate a sweeping magnetic field that steers the beam along a desired raster scan pattern at a target.

Beam Shape Control

M. Yanagisawa, et. al. "Particle Beam Irradiation System and Method of Adjusting Irradiation Field Forming Apparatus", U.S. Pat. No. 7,154,107 (Dec. 26, 2006) and M. Yanagisawa, et. al. "Particle Beam Irradiation System and Method of Adjusting Irradiation Field Forming Apparatus", U.S. Pat. No. 7,049,613 (May 23, 2006) describe a particle therapy system having a scattering compensator and a range modulation wheel. Movement of the scattering compensator and the range modulation wheel adjusts a size of the ion beam and scattering intensity resulting in penumbra control and a more uniform dose distribution to a diseased body part.

T. Haberer, et. al. "Device and Method for Adapting the Size of an Ion Beam Spot in the Domain of Tumor Irradiation", U.S. Pat. No. 6,859,741 (Feb. 22, 2005) describe a method and apparatus for adapting the size of an ion beam in tumor irradiation. Quadrupole magnets determining the size of the ion beam spot are arranged directly in front of raster scanning magnets determining the size of the ion beam spot. The apparatus contains a control loop for obtaining current correction values to further control the ion beam spot size.

K. Matsuda, et. al. "Charged Particle Irradiation Apparatus and an Operating Method Thereof", U.S. Pat. No. 5,986,274 (Nov. 16, 1999) describe a charged particle irradiation apparatus capable of decreasing a lateral dose falloff at boundaries of an irradiation field of a charged particle beam using controlling magnet fields of quadrupole electromagnets and deflection electromagnets to control the center of the charged particle beam passing through the center of a scatterer irrespective of direction and intensity of a magnetic field generated by scanning electromagnets.

K. Hiramoto, et. al. "Charged Particle Beam Apparatus and Method for Operating the Same", U.S. Pat. No. 5,969,367 (Oct. 19, 1999) describe a charged particle beam apparatus where a the charged particle beam is enlarged by a scatterer resulting in a Gaussian distribution that allows overlapping of irradiation doses applied to varying spot positions.

M. Moyers, et. al. "Charged Particle Beam Scattering System", U.S. Pat. No. 5,440,133 (Aug. 8, 1995) describe a radiation treatment apparatus for producing a particle beam and a scattering foil for changing the diameter of the charged particle beam.

C. Nunan "Multileaf Collimator for Radiotherapy Machines", U.S. Pat. No. 4,868,844 (Sep. 19, 1989) describes a radiation therapy machine having a multileaf collimator formed of a plurality of heavy metal leaf bars movable to form a rectangular irradiation field.

R. Maughan, et. al. "Variable Radiation Collimator", U.S. Pat. No. 4,754,147 (Jun. 28, 1988) describe a variable collimator for shaping a cross-section of a radiation beam that relies on rods, which are positioned around a beam axis. The rods are shaped by a shaping member cut to a shape of an area of a patient go be irradiated.

Beam Energy/Intensity

M. Yanagisawa, et. al. "Charged Particle Therapy System, Range Modulation Wheel Device, and Method of Installing Range Modulation Wheel Device", U.S. Pat. No. 7,355,189 (Apr. 8, 2008) and Yanagisawa, et. al. "Charged Particle Therapy System, Range Modulation Wheel Device, and Method of Installing Range Modulation Wheel Device", U.S. Pat. No. 7,053,389 (May 30, 2008) both describe a particle therapy system having a range modulation wheel. The ion beam passes through the range modulation wheel resulting in a plurality of energy levels corresponding to a plurality of stepped thicknesses of the range modulation wheel.

M. Yanagisawa, et. al. "Particle Beam Irradiation System and Method of Adjusting Irradiation Apparatus", U.S. Pat. No. 7,297,967 (Nov. 20, 2007); M. Yanagisawa, et. al. "Particle Beam Irradiation System and Method of Adjusting Irradiation Apparatus", U.S. Pat. No. 7,071,479 (Jul. 4, 2006); M. Yanagisawa, et. al. "Particle Beam Irradiation System and Method of Adjusting Irradiation Apparatus", U.S. Pat. No. 7,026,636 (Apr. 11, 2006); and M. Yanagisawa, et. al. "Particle Beam Irradiation System and Method of Adjusting Irradiation Apparatus", U.S. Pat. No. 6,777,700 (Aug. 17, 2004) all describe a scattering device, a range adjustment device, and a peak spreading device. The scattering device and range adjustment device are combined together and are moved along a beam axis. The spreading device is independently moved along the axis to adjust the degree of ion beam scattering. Combined, the devise increases the degree of uniformity of radiation dose distribution to a diseased tissue.

A. Sliski, et. al. "Programmable Particle Scatterer for Radiation Therapy Beam Formation", U.S. Pat. No. 7,208,748 (Apr. 24, 2007) describe a programmable pathlength of a fluid disposed into a particle beam to modulate scattering angle and beam range in a predetermined manner. The charged particle beam scatterer/range modulator comprises a fluid reservoir having opposing walls in a particle beam path and a drive to adjust the distance between the walls of the fluid reservoir under control of a programmable controller to create a predetermined spread out Bragg peak at a predetermined depth in a tissue. The beam scattering and modulation is continuously and dynamically adjusted during treatment of a tumor to deposit a dose in a targeted predetermined three dimensional volume.

M. Tadokoro, et. al. "Particle Therapy System", U.S. Pat. No. 7,247,869 (Jul. 24, 2007) and U.S. Pat. No. 7,154,108 (Dec. 26, 2006) each describe a particle therapy system capable of measuring energy of a charged particle beam during irradiation during use. The system includes a beam passage between a pair of collimators, an energy detector mounted, and a signal processing unit.

G. Kraft, et. al. "Ion Beam Scanner System and Operating Method", U.S. Pat. No. 6,891,177 (May 10, 2005) describe an ion beam scanning system having a mechanical alignment system for the target volume to be scanned and allowing for depth modulation of the ion beam by means of a linear motor and transverse displacement of energy absorption means resulting in depth-staggered scanning of volume elements of a target volume.

G. Hartmann, et. al. "Method for Operating an Ion Beam Therapy System by Monitoring the Distribution of the Radiation Dose", U.S. Pat. No. 6,736,831 (May 18, 2004) describe a method for operation of an ion beam therapy system having a grid scanner and irradiates and scans an area surrounding an isocentre. Both the depth dose distribution and the transverse dose distribution of the grid scanner device at various positions in the region of the isocentre are measured and evaluated.

Y. Jongen "Method for Treating a Target Volume with a Particle Beam and Device Implementing Same", U.S. Pat. No. 6,717,162 (Apr. 6, 2004) describes a method of producing from a particle beam a narrow spot directed towards a target volume, characterized in that the spot sweeping speed and particle beam intensity are simultaneously varied.

G. Kraft, et. al. "Device for Irradiating a Tumor Tissue", U.S. Pat. No. 6,710,362 (Mar. 23, 2004) describe a method and apparatus of irradiating a tumor tissue, where the apparatus has an electromagnetically driven ion-braking device in the proton beam path for depth-wise adaptation of the proton beam that adjusts both the ion beam direction and ion beam range.

K. Matsuda, et. al. "Charged Particle Beam Irradiation Apparatus", U.S. Pat. No. 6,617,598 (Sep. 9, 2003) describe a charged particle beam irradiation apparatus that increased the width in a depth direction of a Bragg peak by passing the Bragg peak through an enlarging device containing three ion beam components having different energies produced according to the difference between passed positions of each of the filter elements.

H. Stelzer, et. al. "Ionization Chamber for Ion Beams and Method for Monitoring the Intensity of an Ion Beam", U.S. Pat. No. 6,437,513 (Aug. 20, 2002) describe an ionization chamber for ion beams and a method of monitoring the intensity of an ion therapy beam. The ionization chamber includes a chamber housing, a beam inlet window, a beam outlet window, a beam outlet window, and a chamber volume filled with counting gas.

H. Akiyama, et. al. "Charged-Particle Beam Irradiation Method and System", U.S. Pat. No. 6,433,349 (Aug. 13, 2002) and H. Akiyama, et. al. "Charged-Particle Beam Irradiation Method and System", U.S. Pat. No. 6,265,837 (Jul. 24, 2001) both describe a charged particle beam irradiation system that includes a changer for changing energy of the particle and an intensity controller for controlling an intensity of the charged-particle beam.

Y. Pu "Charged Particle Beam Irradiation Apparatus and Method of Irradiation with Charged Particle Beam", U.S. Pat. No. 6,034,377 (Mar. 7, 2000) describes a charged particle beam irradiation apparatus having an energy degrader comprising: (1) a cylindrical member having a length; and (2) a distribution of wall thickness in a circumferential direction around an axis of rotation, where thickness of the wall determines energy degradation of the irradiation beam.

Dosage

K. Matsuda, et. al. "Particle Beam Irradiation System", U.S. Pat. No. 7,372,053 (Nov. 27, 2007) describe a particle beam irradiation system ensuring a more uniform dose distribution at an irradiation object through use of a stop signal, which stops the output of the ion beam from the irradiation device.

H. Sakamoto, et. al. "Radiation Treatment Plan Making System and Method", U.S. Pat. No. 7,054,801 (May 30, 2006) describe a radiation exposure system that divides an exposure region into a plurality of exposure regions and uses a radiation simulation to plan radiation treatment conditions to obtain flat radiation exposure to the desired region.

G. Hartmann, et. al. "Method For Verifying the Calculated Radiation Dose of an Ion Beam Therapy System", U.S. Pat. No. 6,799,068 (Sep. 28, 2004) describe a method for the verification of the calculated dose of an ion beam therapy system that comprises a phantom and a discrepancy between the calculated radiation dose and the phantom.

H. Brand, et. al. "Method for Monitoring the Irradiation Control of an Ion Beam Therapy System", U.S. Pat. No. 6,614,038 (Sep. 2, 2003) describe a method of checking a calculated irradiation control unit of an ion beam therapy system, where scan data sets, control computer parameters, measuring sensor parameters, and desired current values of scanner magnets are permanently stored.

T. Kan, et. al. "Water Phantom Type Dose Distribution Determining Apparatus", U.S. Pat. No. 6,207,952 (Mar. 27, 2001) describe a water phantom type dose distribution apparatus that includes a closed water tank, filled with water to the brim, having an inserted sensor that is used to determine an actual dose distribution of radiation prior to radiation therapy.

Starting/Stopping Irradiation

K. Hiramoto, et. al. "Charged Particle Beam Apparatus and Method for Operating the Same", U.S. Pat. No. 6,316,776 (Nov. 13, 2001) describe a charged particle beam apparatus where a charged particle beam is positioned, started, stopped, and repositioned repetitively. Residual particles are used in the accelerator without supplying new particles if sufficient charge is available.

K. Matsuda, et. al. "Method and Apparatus for Controlling Circular Accelerator", U.S. Pat. No. 6,462,490 (Oct. 8, 2002) describe a control method and apparatus for a circular accelerator for adjusting timing of emitted charged particles. The clock pulse is suspended after delivery of a charged particle stream and is resumed on the basis of state of an object to be irradiated.

Movable Patient

N. Rigney, et. al. "Patient Alignment System with External Measurement and Object Coordination for Radiation Therapy System", U.S. Pat. No. 7,199,382 (Apr. 3, 2007) describe a patient alignment system for a radiation therapy system that includes multiple external measurement devices that obtain position measurements of movable components of the radiation therapy system. The alignment system uses the external measurements to provide corrective positioning feedback to more precisely register the patient to the radiation beam.

Y. Muramatsu, et. al. "Medical Particle Irradiation Apparatus", U.S. Pat. No. 7,030,396 (Apr. 18, 2006); Y. Muramatsu, et. al. "Medical Particle Irradiation Apparatus", U.S. Pat. No. 6,903,356 (Jun. 7, 2005); and Y. Muramatsu, et. al. "Medical Particle Irradiation Apparatus", U.S. Pat. No. 6,803,591 (Oct. 12, 2004) all describe a medical particle irradiation apparatus having a rotating gantry, an annular frame located within the gantry such that is can rotate relative to the rotating gantry, an anti-correlation mechanism to keep the frame from rotating with the gantry, and a flexible moving floor engaged with the frame is such a manner to move freely with a substantially level bottom while the gantry rotates.

H. Nonaka, et. al. "Rotating Radiation Chamber for Radiation Therapy", U.S. Pat. No. 5,993,373 (Nov. 30, 1999) describe a horizontal movable floor composed of a series of multiple plates that are connected in a free and flexible manner, where the movable floor is moved in synchrony with rotation of a radiation beam irradiation section.

Respiration

K. Matsuda "Radioactive Beam Irradiation Method and Apparatus Taking Movement of the Irradiation Area Into Consideration", U.S. Pat. No. 5,538,494 (Jul. 23, 1996) describes a method and apparatus that enables irradiation even in the case of a diseased part changing position due to physical activity, such as breathing and heart beat. Initially, a position change of a diseased body part and physical activity of the patient are measured concurrently and a relationship therebetween is defined as a function. Radiation therapy is performed in accordance to the function.

Patient Positioning

Y. Nagamine, et. al. "Patient Positioning Device and Patient Positioning Method", U.S. Pat. Nos. 7,212,609 and 7,212,608 (May 1, 2007) describe a patient positioning system that compares a comparison area of a reference X-ray image and a current X-ray image of a current patient location using pattern matching.

D. Miller, et. al. "Modular Patient Support System", U.S. Pat. No. 7,173,265 (Feb. 6, 2007) describe a radiation treatment system having a patient support system that includes a modularly expandable patient pod and at least one immobilization device, such as a moldable foam cradle.

K. Kato, et. al. "Multi-Leaf Collimator and Medical System Including Accelerator", U.S. Pat. No. 6,931,100 (Aug. 16, 2005); K. Kato, et. al. "Multi-Leaf Collimator and Medical System Including Accelerator", U.S. Pat. No. 6,823,045 (Nov. 23, 2004); K. Kato, et. al. "Multi-Leaf Collimator and Medical System Including Accelerator", U.S. Pat. No. 6,819,743 (Nov. 16, 2004); and K. Kato, et. al. "Multi-Leaf Collimator and Medical System Including Accelerator", U.S. Pat. No. 6,792,078 (Sep. 14, 2004) all describe a system of leaf plates used to shorten positioning time of a patient for irradiation therapy. Motor driving force is transmitted to a plurality of leaf plates at the same time through a pinion gear. The system also uses upper and lower air cylinders and upper and lower guides to position a patient.

Imaging

P. Adamee, et. al. "Charged Particle Beam Apparatus and Method for Operating the Same", U.S. Pat. No. 7,274,018 (Sep. 25, 2007) and P. Adamee, et. al. "Charged Particle Beam Apparatus and Method for Operating the Same", U.S. Pat. No. 7,045,781 (May 16, 2006) describe a charged particle beam apparatus configured for serial and/or parallel imaging of an object.

K. Hiramoto, et. al. "Ion Beam Therapy System and its Couch Positioning System", U.S. Pat. No. 7,193,227 (Mar. 20, 2007) describe a ion beam therapy system having an X-ray imaging system moving in conjunction with a rotating gantry.

C. Maurer, et. al. "Apparatus and Method for Registration of Images to Physical Space Using a Weighted Combination of Points and Surfaces", U.S. Pat. No. 6,560,354 (May 6, 2003) described a process of X-ray computed tomography registered to physical measurements taken on the patient's body, where different body parts are given different weights. Weights are used in an iterative registration process to determine a rigid body transformation process, where the transformation function is used to assist surgical or stereotactic procedures.

M. Blair, et. al. "Proton Beam Digital Imaging System", U.S. Pat. No. 5,825,845 (Oct. 20, 1998) describe a proton beam digital imaging system having an X-ray source that is movable into the treatment beam line that can produce an X-ray beam through a region of the body. By comparison of the relative positions of the center of the beam in the patient orientation image and the isocentre in the master prescription image with respect to selected monuments, the amount and direction of movement of the patient to make the best beam center correspond to the target isocentre is determined.

S. Nishihara, et. al. "Therapeutic Apparatus", U.S. Pat. No. 5,039,867 (Aug. 13, 1991) describe a method and apparatus for positioning a therapeutic beam in which a first distance is determined on the basis of a first image, a second distance is determined on the basis of a second image, and the patient is moved to a therapy beam irradiation position on the basis of the first and second distances.

Problem

There exists in the art of particle beam treatment of cancerous tumors in the body a need for efficient acceleration of charged particles in a synchrotron of a charged particle therapy system. Further, there exists in the art of particle beam therapy of cancerous tumors a need for extraction of charged particles at a specified energy, time, and/or intensity to yield a charged particle beam for efficient, precise, and accurate noninvasive, in-vivo treatment of a solid cancerous tumor with minimization of damage to surrounding healthy tissue in a patient. Still further, there exists a need in the art to continue acceleration of charged particles in a synchrotron during the extraction process.

SUMMARY OF THE INVENTION

The invention comprises a charged particle beam acceleration and optional extraction method and apparatus used as part of a charged particle beam radiation therapy system.

DETAILED DESCRIPTION OF THE INVENTION

Figure 1:
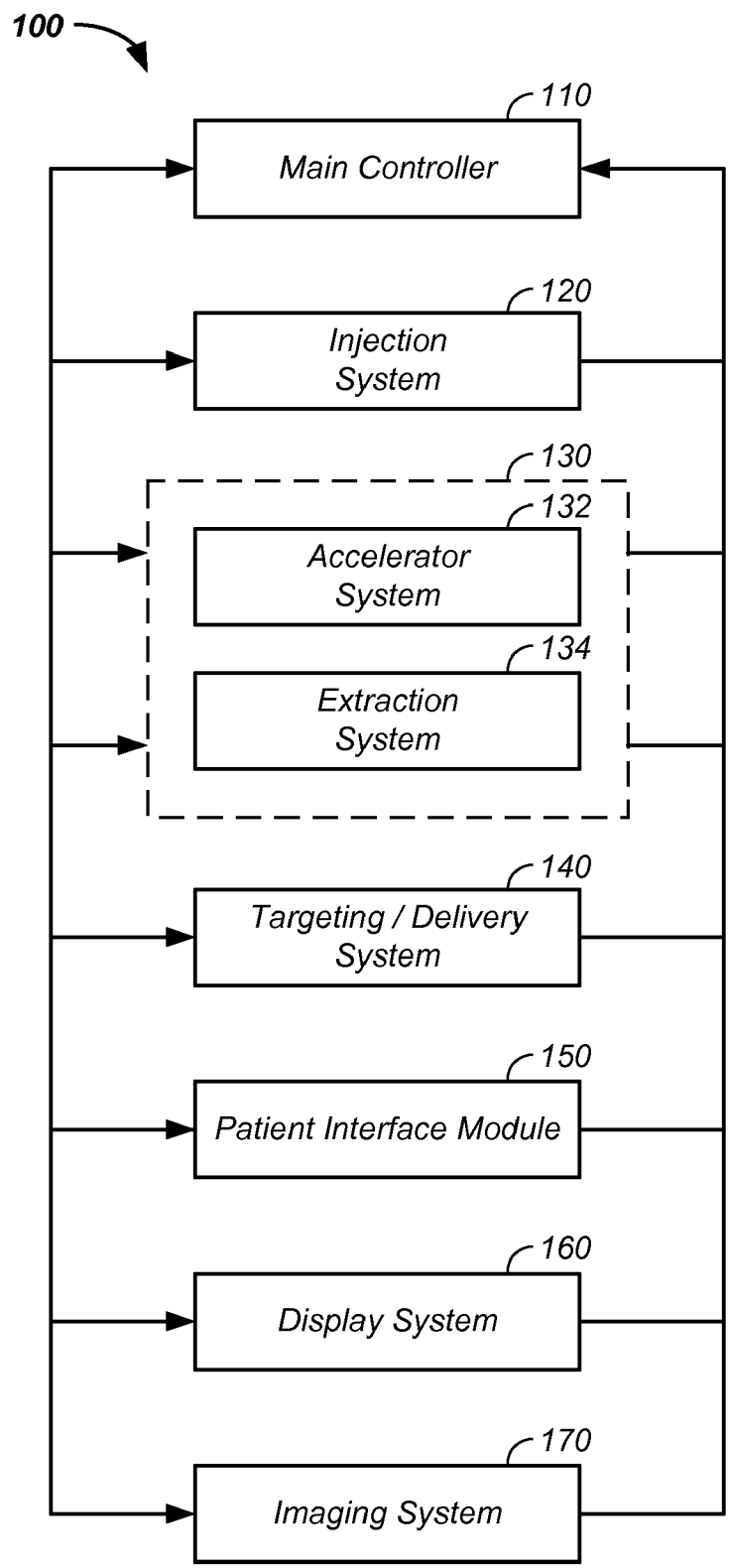
FIG. 1 illustrates component connections of a particle beam therapy system.

The invention comprises a charged particle beam acceleration and optional extraction method and apparatus used in conjunction with charged particle beam radiation therapy of cancerous tumors.

Novel design features of a synchrotron are described. Particularly, turning magnets, focusing magnets, and extraction elements are described that minimize the overall size of the synchrotron, provide a tightly controlled proton beam, directly reduce the size of required magnetic fields, directly reduces required operating power, and allow continual acceleration of protons in a synchrotron even during a process of extracting protons from the synchrotron.

Cyclotron/Synchrotron

A cyclotron uses a constant magnetic field and a constant-frequency applied electric field. One of the two fields is varied in a synchrocyclotron. Both of these fields are varied in a synchrotron. Thus, a synchrotron is a particular type of cyclic particle accelerator in which a magnetic field is used to turn the particles so they circulate and an electric field is used to accelerate the particles. The synchroton carefully synchronizes the applied fields with the travelling particle beam.

By increasing the fields appropriately as the particles gain energy, the charged particles path can be held constant as they are accelerated. This allows the vacuum container for the particles to be a large thin torus. In reality it is easier to use some straight sections between the bending magnets and some turning sections giving the torus the shape of a round-cornered polygon. A path of large effective radius is thus constructed using simple straight and curved pipe segments, unlike the disc-shaped chamber of the cyclotron type devices. The shape also allows and requires the use of multiple magnets to bend the particle beam.

The maximum energy that a cyclic accelerator can impart is typically limited by the strength of the magnetic fields and the minimum radius/maximum curvature, of the particle path. In a cyclotron the maximum radius is quite limited as the particles start at the center and spiral outward, thus this entire path must be a self-supporting disc-shaped evacuated chamber. Since the radius is limited, the power of the machine becomes limited by the strength of the magnetic field. In the case of an ordinary electromagnet, the field strength is limited by the saturation of the core because when all magnetic domains are aligned the field may not be further increased to any practical extent. The arrangement of the single pair of magnets also limits the economic size of the device.

Synchrotrons overcome these limitations, using a narrow beam pipe surrounded by much smaller and more tightly focusing magnets. The ability of this device to accelerate particles is limited by the fact that the particles must be charged to be accelerated at all, but charged particles under acceleration emit photons, thereby losing energy. The limiting beam energy is reached when the energy lost to the lateral acceleration required to maintain the beam path in a circle equals the energy added each cycle. More powerful accelerators are built by using large radius paths and by using more numerous and more powerful microwave cavities to accelerate the particle beam between corners. Lighter particles, such as electrons, lose a larger fraction of their energy when turning. Practically speaking, the energy of electron/positron accelerators is limited by this radiation loss, while it does not play a significant role in the dynamics of proton or ion accelerators. The energy of those is limited strictly by the strength of magnets and by the cost.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any charged particle beam system is equally applicable to the techniques described herein.

Referring now to FIG. 1, a charged particle beam system 100 is illustrated. The charged particle beam preferably comprises a number of subsystems including any of: a main controller 110; an injection system 120; a synchrotron 130 that typically includes: (1) an accelerator system 132 and (2) an extraction system 134; a targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the targeting/delivery system 140 to the patient interface module 150. One or more components of the patient interface module 150 are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path; however, cyclotrons are alternatively used, albeit with their inherent limitations of energy, intensity, and extraction control. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central point or region.

Figure 2:
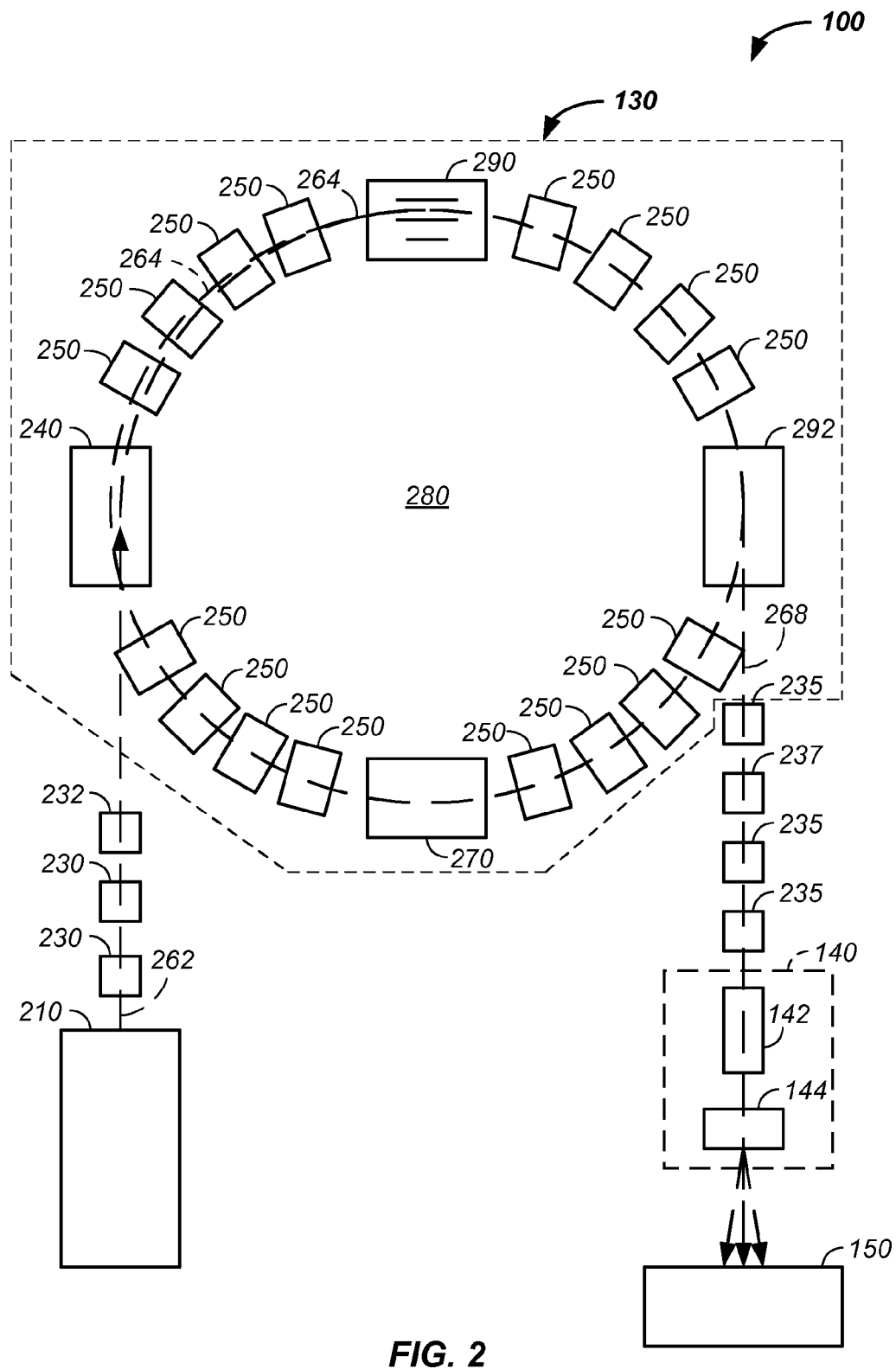
FIG. 2 illustrates a charged particle therapy system.

Referring now to FIG. 2, an illustrative exemplary embodiment of one version of the charged particle beam system 100 is provided. In the illustrated embodiment, a charged particle beam source 210 generates protons. The protons are delivered into a vacuum tube that runs into, through, and out of the synchrotron. The generated protons are delivered along an initial path 262. Focusing magnets 230, such as quadrupole magnets, are used to focus the proton beam path. The focused protons having an initial energy are introduced into an inflector 240. Typically, the initial beam path 262 is along an axis off of, such as above, a circulating plane of the synchrotron 130. The inflector 240 moves the protons into the synchrotron 130. Circulating magnets 250 are used to turn the protons along a circulating beam path 264. The circulating magnets 250 bend the initial beam path 262 into a circulating beam path 264. In this example, the circulating magnets 250 are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the circulating magnets 250 to maintain stable circulation of the protons about a central point or region 280 of the synchrotron. At separate points in time the accelerator 270/circulating magnet 250 combination is used to accelerate and/or decelerate the circulating protons while maintaining the protons in the circulating path or orbit. An extraction system 290 is used in combination with a deflector 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using focusing magnets 230, such as quadrupole magnets along a transport path 268 into the targeting/delivery system 140. Two components of a targeting system 140 typically include a first axis control 142, such as a vertical control, and a second axis control 144, such as a horizontal control. Protons are delivered with control to the patient interface module 150 and to a tumor of a patient.

Circulating System

A synchrotron 130 preferably comprises a combination of straight sections 310 and ion beam turning sections 320. Hence, the circulating path of the protons is not circular in a synchrotron, but is rather a polygon with rounded corners.

In one illustrative embodiment, the synchrotron 130, which as also referred to as an accelerator system, has four straight elements and four turning sections. Examples of straight sections 310 include the: inflector 240, accelerator 270, extraction system 290, and deflector 292. Along with the four straight sections are four ion beam turning sections 320, which are also referred to as magnet sections or turning sections. Turning sections are further described, infra.

Figure 3:
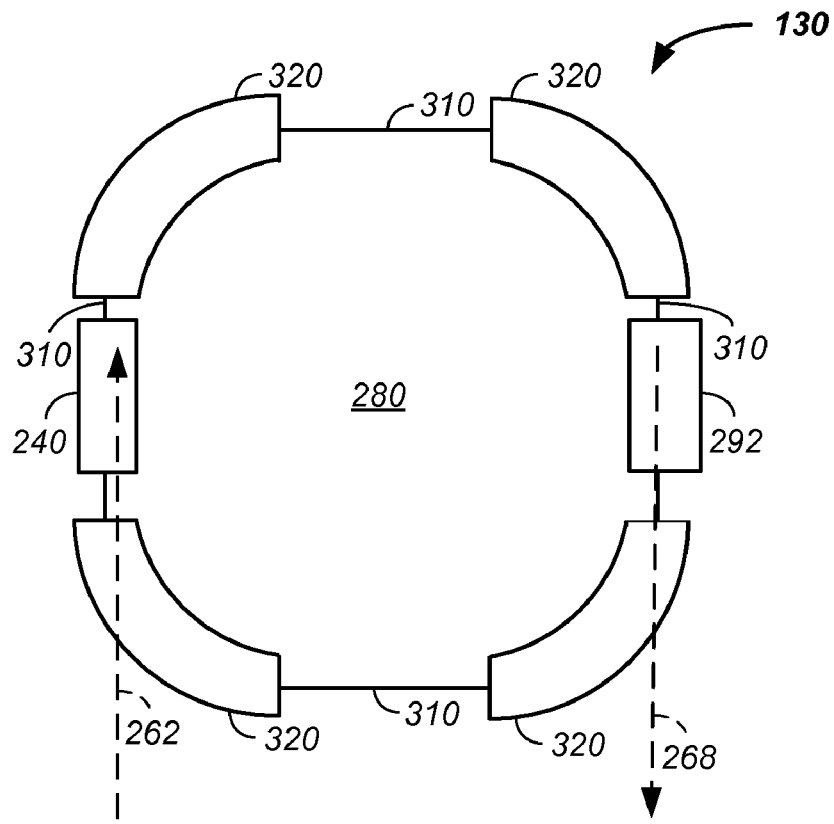
FIG. 3 illustrates straight and turning sections of a synchrotron.

Referring now to FIG. 3, an exemplary synchrotron is illustrated. In this example, protons delivered along the initial path 262 are inflected into the circulating beam path with the inflector 240 and after acceleration are extracted via a deflector 292 to a beam transport path 268. In this example, the synchrotron 130 comprises four straight sections 310 and four turning sections 320 where each of the four turning sections use one or more magnets to turn the proton beam about ninety degrees. As is further described, infra, the ability to closely space the turning sections and efficiently turn the proton beam results in shorter straight sections. Shorter straight sections allows for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross sectional diameters for systems using a quadrupole focusing magnet in the circulating proton beam path.

Figure 4:
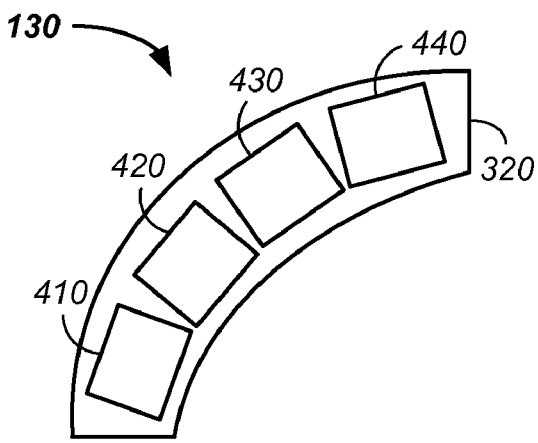
FIG. 4 illustrates turning magnets of a synchrotron.

Referring now to FIG. 4, additional description of the first turning section 320 is provided. Each of the turning sections preferably comprises multiple magnets, such as about 2, 4, 6, 8, 10, or 12 magnets. In this example, four turning magnets 410, 420, 430, 440 in the first turning section 320 are used to illustrate key principles, which are the same regardless of the number of magnets in a turning section 320. A turning magnet 410 is a particular type of circulating magnet 250.

In physics, the Lorentz force is the force on a point charge due to electromagnetic fields. The Lorentz force is given by the equation 1 in terms of magnetic fields with the election field terms not included.

$$F = q(v \times B) \qquad \text{eq. 1}$$

In equation 1, F is the force in newtons; B is the magnetic field in Teslas; and v is the instantaneous velocity of the particles in meters per second.

Figure 5:
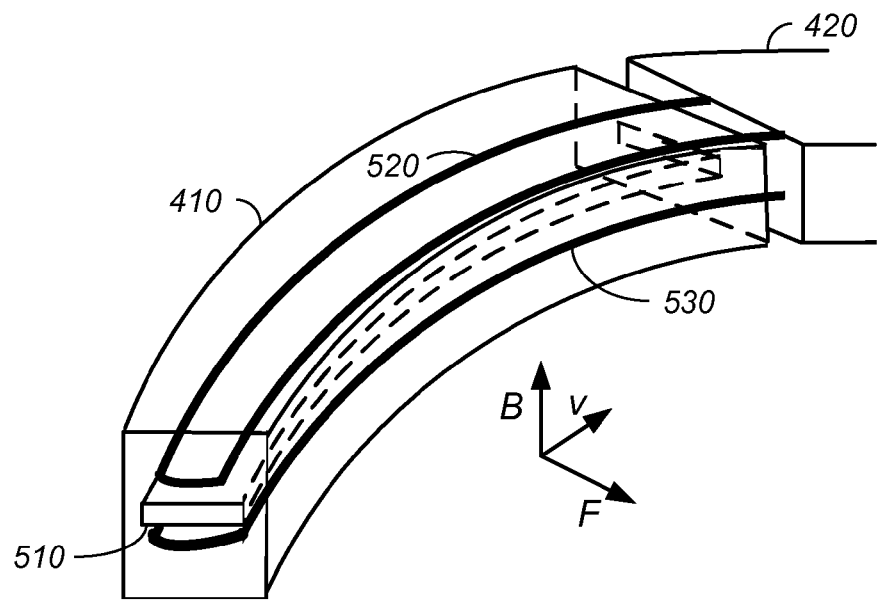
FIG. 5 provides a perspective view of a turning magnet.

Referring now to FIG. 5, an example of a single magnet turning section 410 is expanded. The turning section includes a gap 510. The gap is preferably a flat gap, allowing for a magnetic field across the gap that is more uniform, even, and intense. The gap 510 runs in a vacuum tube between two magnet halves. The gap is controlled by at least two parameters: (1) the gap 510 is kept as large as possible to minimize loss of protons and (2) the gap 510 is kept as small as possible to minimize magnet sizes and the associated size and power requirements of the magnet power supplies. The flat nature of the gap 510 allows for a compressed and more uniform magnetic field across the gap. One example of a gap dimension is to accommodate a vertical proton beam size of about 2 cm with a horizontal beam size of about 5 to 6 cm.

As described, supra, a larger gap size requires a larger power supply. For instance, if the gap size doubles in vertical size, then the power supply requirements increase by about a factor of 4. The flatness of the gap is also important. For example, the flat nature of the gap allows for an increase in energy of the extracted protons from about 250 to about 330 MeV. More particularly, if the gap 510 has an extremely flat surface, then the limits of a magnetic field of an iron magnet are reachable. An exemplary precision of the flat surface of the gap 510 is a polish of less than about 5 microns and preferably with a polish of about 1 to 3 microns. Unevenness in the surface results in imperfections in the applied magnetic field. The polished flat surface spreads unevenness of the applied magnetic field.

Still referring to FIG. 5, the charged particle beam moves through the gap with an instantaneous velocity, v. A first magnetic coil 520 and a second magnetic coil 530 run above and below the gap 510, respectively. Current running through the coils 520, 530 results in a magnetic field, B, running through the single magnet turning section 410. In this example, the magnetic field, B, runs upward, which results in a force, F, pushing the charged particle beam inward toward a central point of the synchrotron, which turns the charged particle beam in an arc.

Figure 7:
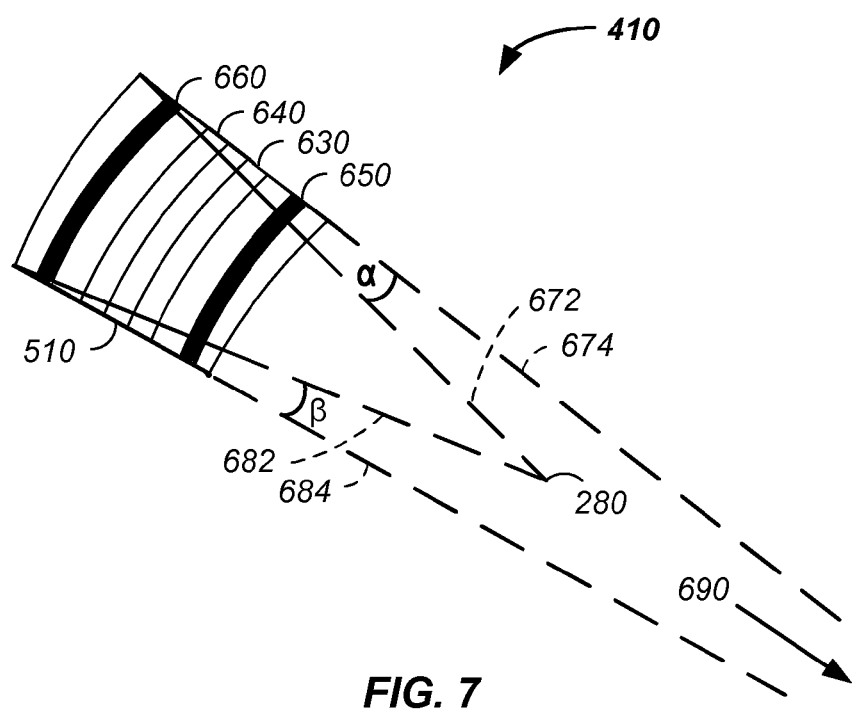
FIG. 7 illustrates a cross sectional view of a turning magnet.
Figure 6:
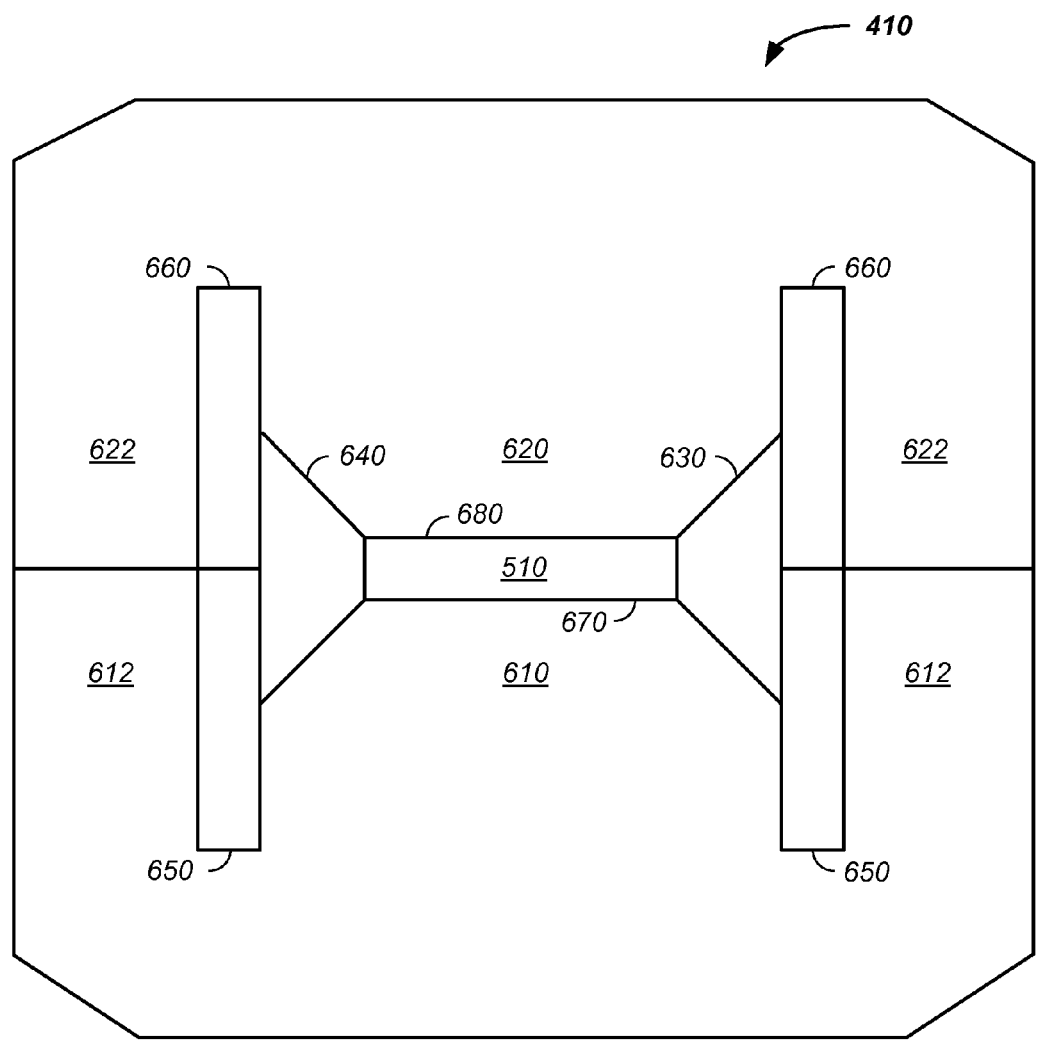
FIG. 6 illustrates a cross sectional view of a turning magnet.

Referring now to FIGS. 6 and 7, two illustrative 90 degree rotated cross-sections of single magnet turning sections 410 are presented. The magnet assembly has a first magnet 610 and a second magnet 620. A magnetic field induced by coils, described infra, runs between the first magnet 610 to the second magnet 620 across the gap 510. Return magnetic fields run through a first yoke 612 and second yoke 622. The charged particles run through the vacuum tube in the gap. As illustrated, protons run into FIG. 6 through the gap 510 and the magnetic field, illustrated as vector B, applies a force F to the protons pushing the protons towards the center of the synchrotron, which is off page to the right in FIG. 6. The magnetic field is created using windings. A first coil making up a first winding coil 650, illustrated as dots in FIG. 6 to representatively present cross sections of the wire for individual windings and illustrated as individual windings in FIG. 7. The second coil of wire making up a second winding 660 is similarly illustratively represented. Isolating gaps 630, 640, such as air gaps, isolate the iron based yokes from the gap 510. The gap is approximately flat to yield a uniform magnetic field across the gap, as described supra.

Still referring to FIG. 7, the ends of a single turning magnet are beveled. Nearly perpendicular or right angle edges of a turning magnet 410 are represented by a dashed lines 674, 684. Preferably, the edge of the turning magnet is beveled at angles alpha, α, and beta, β, which is the off perpendicular angle between the right angles 674, 684 and beveled edges 672, 682. The angle alpha is used to describe the effect and the description of angle alpha applies to angle beta, but angle alpha is optionally different from angle beta. The angle alpha provides an edge focusing effect. Beveling the edge of the turning magnet 410 at angle alpha focuses the proton beam.

Multiple turning magnets provide multiple edge focusing effects in the synchrotron 310. If only one turning magnet is used, then the beam is only focused once for angle alpha or twice for angle alpha and angle beta. However, by using smaller turning magnets, more turning magnets fit into the turning sections 320 of the synchrotron 310. For example, if four magnets are used in a turning section 320 of the synchrotron, then there are eight possible edge focusing effect surfaces, two edges per magnet. The eight focusing surfaces yield a smaller cross sectional beam size. This allows the use of a smaller gap 510.

The use of multiple edge focusing effects in the turning magnets results in not only a smaller gap, but also the use of smaller magnets and smaller power supplies. For a synchrotron 310 having four turning sections 320 where each turning sections has four turning magnets and each turning magnet has two focusing edges, a total of thirty-two focusing edges exist for each orbit of the protons in the circulating path of the synchrotron 310. Similarly, if 2, 6, or 8 magnets are used in a given turning section, or if 2, 3, 5, or 6 turning sections are used, then the number of edge focusing surfaces expands or contracts according to equation 2.

$$TFE = NTS * \frac{M}{NTS} * \frac{FE}{M} \qquad \text{eq. 2}$$

where TFE is the number of total focusing edges, NTS is the number of turning section, M is the number of magnets, and FE is the number of focusing edges. Naturally, not all magnets are necessarily beveled.

The inventors have determined that multiple smaller magnets have benefits over fewer larger magnets. For example, the use of 16 small magnets yields 32 focusing edges whereas the use of 4 larger magnets yields only 8 focusing edges. The use of a synchrotron having more focusing edges results in a circulating path of the synchrotron built without the use of focusing quadrupoles magnets. All prior art synchrotrons use quadrupoles in the circulating path of the synchrotron. Further, the use of quadrupoles in the circulating path necessitates additional straight sections in the circulating path of the synchrotron. Thus, the use of quadrupoles in the circulating path of a synchrotron results in synchrotrons having larger diameters or larger circumferences. Further, the inventors have determined that having coil wrapped around at least two of the turning magnets reduces space requirements between turning magnets. The reduction in space between the turning magnets yields a higher percentage of the circulating acceleration path that is being focused or bent by the focusing and bending magnets. Hence, the synchrotron can be made with a smaller circulating path, such as less than sixty meters by having the coils not occupy space directly between at least two of the turning magnets.

In various embodiments of the system described herein, the synchrotron has:
- at least 4 and preferably 6, 8, 10 or more edge focusing edges per 90 degrees of turn of the charged particle beam in a synchrotron having four turning sections;
- at least about 16 and preferably about 24, 32, or more edge focusing edges per orbit of the charged particle beam in the synchrotron;
- only 4 turning sections where each of the turning sections includes at least 4 and preferably 8 edge focusing edges;
- an equal number of straight sections and turning sections;
- exactly 4 turning sections;
- at least 4 edge focusing edges per turning section;
- no quadrupoles in the circulating path of the synchrotron;
- a rounded corner rectangular polygon configuration;
- a circumference of less than 60 meters;
- a circumference of less than 60 meters and 32 edge focusing surfaces; and/or
- any of about 8, 16, 24, or 32 non-quadrupoles magnets per circulating path of the synchrotron, where the non-quadrupole magnets include edge focusing edges.

Referring now to FIG. 6, the incident surface 670 of the first magnet 610 is further described. FIG. 6 is not to scale and is illustrative in nature. Local imperfections or unevenness in quality of the finish of the incident surface 670 results in inhomogeneities or imperfections in the magnetic field applied to the gap 510. Preferably, the incident surface 670 is flat, such as to within about a zero to three micron finish polish, or less preferably to about a ten micron finish polish.

Proton Beam Extraction

Figure 8:
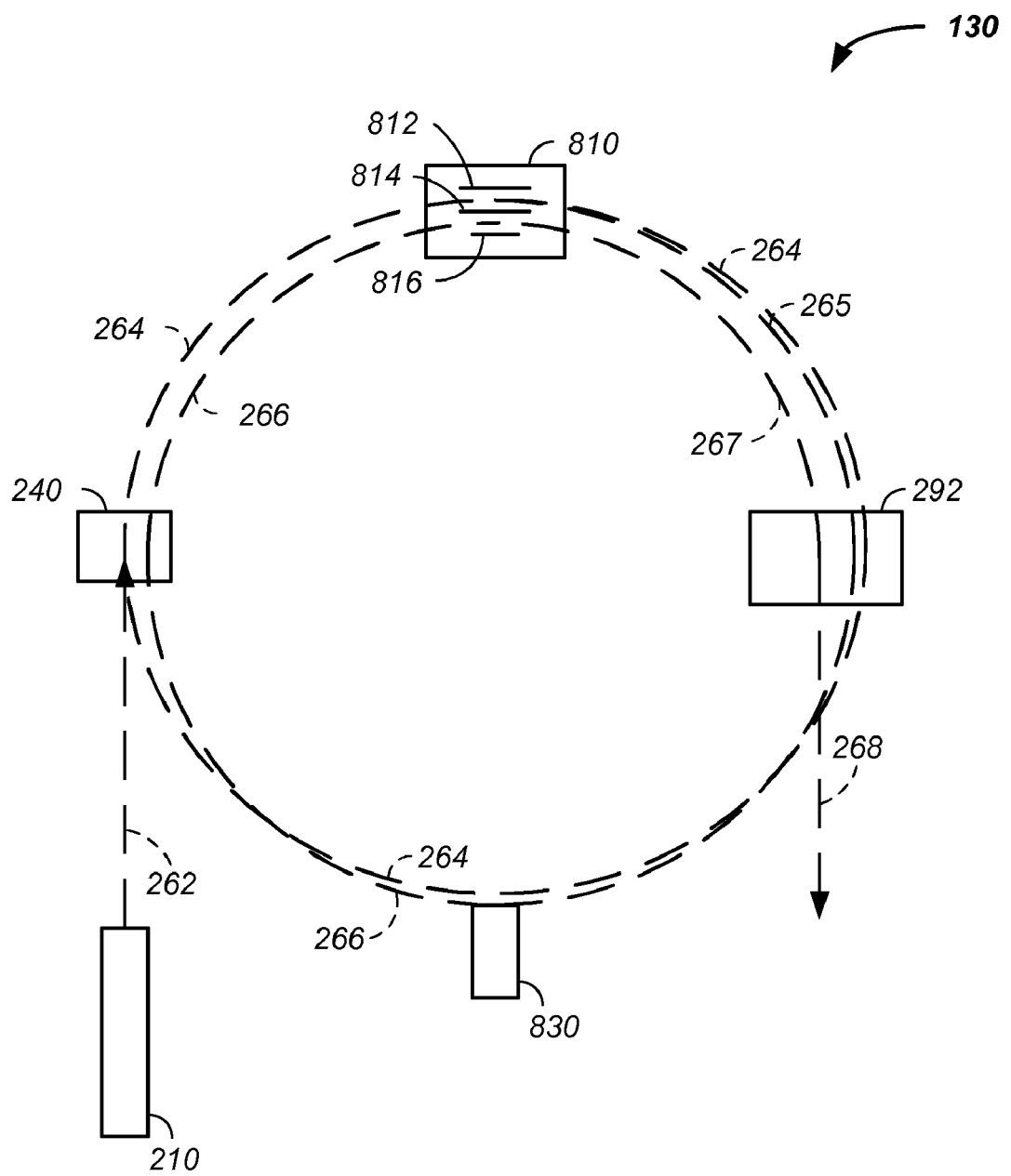
FIG. 8 illustrates a charged particle extraction system.

Referring now to FIG. 8, an exemplary proton extraction process from the synchrotron 130 is illustrated. For clarity, FIG. 8 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of turning magnets 250. The circulating path is referred to herein as an original central beamline 264. The protons repeatedly cycle around a central point in the synchrotron 280. The proton path traverses through an RF cavity system 310. To initiate extraction, an RF field is applied across a first blade 812 and a second blade 814, in the RF cavity system 810. The first blade 812 and second blade 814 are referred to herein as a first pair of blades.

In the proton extraction process, an RF voltage is applied across the first pair of blades, where the first blade 812 of the first pair of blades is on one side of the circulating proton beam path 264 and the second blade 814 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265.

With a sufficient sine wave betatron amplitude, the altered circulating beam path 265 touches a material 830, such as a foil or a sheet of foil. The foil is preferably a lightweight material, such as beryllium, a lithium hydride, a carbon sheet, or a material of low nuclear charge. A material of low nuclear charge is a material composed of atoms consisting essentially of atoms having six or fewer protons. The foil is preferably about 10 to 150 microns thick, is more preferably 30 to 100 microns thick, and is still more preferably 40-60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 830 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades. In one case, the second pair of blades is physically distinct and/or are separated from the first pair of blades. In a second case, one of the first pair of blades is also a member of the second pair of blades. For example, the second pair of blades is the second blade 814 and a third blade 816 in the RF cavity system 810. A high voltage DC signal, such as about 1 to 5 kV, is then applied across the second pair of blades, which directs the protons out of the synchrotron through a deflector 292, such as a Lamberson magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time.

The benefits of the system include a multi-dimensional scanning system. Particularly, the system allows an energy change while scanning. Because the extraction system does not depend on any change any change in magnetic field properties, it allows the synchrotron to continue to operate in acceleration or deceleration mode during the extraction process. Stated differently, the extraction process does not interfere with synchrotron. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time.

Proton Beam Position Control

Figure 9:
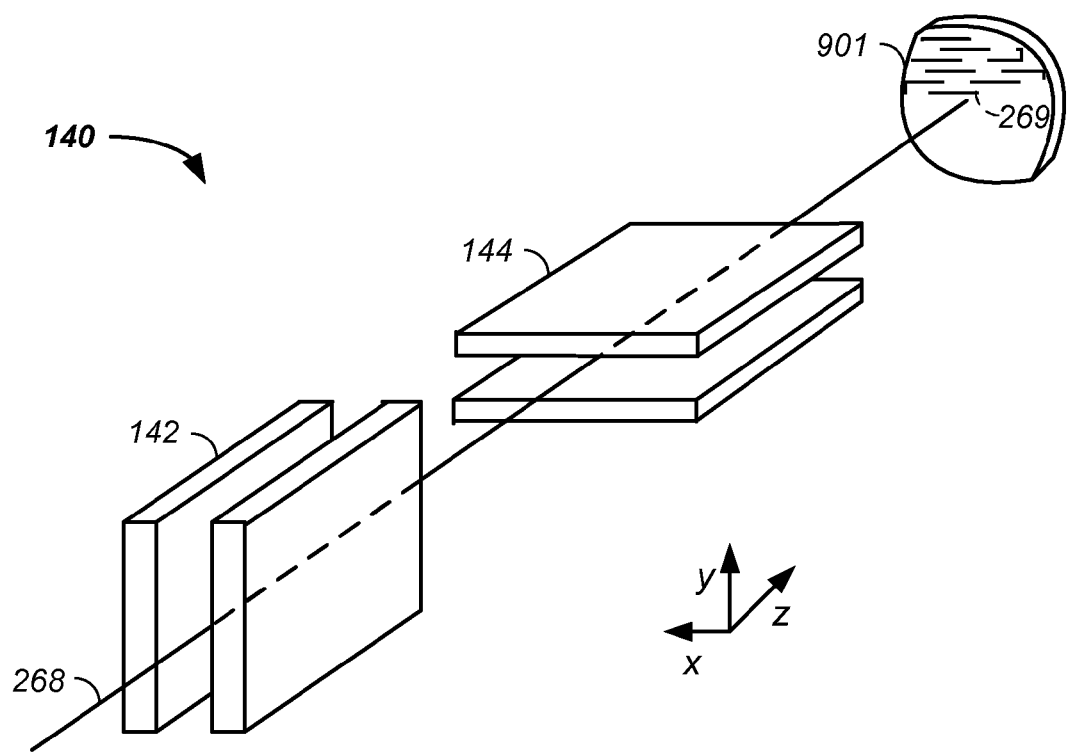
FIG. 9 illustrates 3-dimensional scanning of a proton beam focal spot.

Referring now to FIG. 9, a beam delivery and tissue volume scanning system is illustrated. Presently, the worldwide radiotherapy community uses a method of dose field forming using a pencil beam scanning system. In stark contrast, FIG. 9 illustrates a spot scanning system or tissue volume scanning system. In the tissue volume scanning system, the proton beam is controlled, in terms of transportation and distribution, using an inexpensive and precise scanning system. The scanning system is an active system, where the beam is focused into a spot focal point of about one-half, one, two, or three millimeters in diameter. The focal point is translated along two axes while simultaneously altering the applied energy of the proton beam, which effectively changes the third dimension of the focal point. For example, in the illustrated system in FIG. 9, the spot is translated up a vertical axis using a vertical scanning magnet 142, is moved horizontally using a horizontal scanning magnet 144, and is then translated down a vertical axis. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor. Combined, the three axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to 200 Hz; and (2) a horizontal amplitude of about 700 mm amplitude and frequency up to 1 Hz. More or less amplitude in each axis is possible by altering the scanning magnet systems.

In FIG. 9, the proton beam goes along an z-axis controlled by the beam energy, the horizontal movement is a x-axis, and the vertical direction is a y-axis. The distance the protons move along the z-axis into the tissue, in this example, is controlled by the kinetic energy of the proton. This coordinate system is arbitrary and exemplary. The actual control of the proton beam is controlled in 3-dimensional space using two scanning magnet systems and by controlling the kinetic energy of the proton beam. The use of the extraction system, described supra, allows for different scanning patterns. Particularly, the system allow simultaneous adjustment of the x-, y-, and z-axes in the irradiation of the solid tumor. The instant position of the targeted charged particle beam is illustrated as the vector 269 striking the tumor 901. Stated again, instead of scanning along an x-, y-plane and then adjusting energy of the protons, such as with a range modulation wheel, the system allows for moving along the z-axes while simultaneously adjusting the x- and or y-axes. Hence, rather than irradiating slices of the tumor, the tumor is optionally irradiated in three simultaneous dimensions. For example, the tumor is irradiated around an outer edge of the tumor in three dimensions. Then the tumor is irradiated around an outer edge of an internal section of the tumor. This process is repeated until the entire tumor is irradiated. This system allows for maximum efficiency of deposition of protons to the tumor 901, as defined using the Bragg peak, to the tumor itself with minimal delivery of proton energy to surrounding healthy tissue.

Combined, the system allows for multi-axes control of the charged particle beam system in a small space with low power supply. For example, the system uses multiple magnets where each magnet has at least one edge focusing effect in each turning section of the synchrotron. The multiple edge focusing effects in the circulating beam path of the synchrotron yield a synchrotron having:

a small circumference system, such as less than about 50 meters;
a vertical proton beam size gap of about 2 cm;
corresponding reduced power supply requirements associated with the reduced gap size;

an extraction system not requiring a newly introduced magnetic field;
acceleration or deceleration of the protons during extraction; and
control of z-axis energy during extraction.

The result is a 3-dimensional scanning system, x-, y-, and z-axes control, where the z-axes control resides in the synchrotron and where the z-axes energy is variably controlled during the extraction process inside the synchrotron.

Proton Beam Therapy Synchronization with Breathing

In another embodiment, delivery of a proton beam dosage is synchronized with a breathing pattern of a subject. When a subject, also referred to herein as a patient, is breathing many portions of the body move with each breath. For example, when a subject breathes the lungs move as do relative positions of organs within the body, such as the stomach, kidneys, liver, chest muscles, skin, heart, and lungs. Generally, most or all parts of the torso move with each breath. Indeed, the inventors have recognized that in addition to motion of the torso with each breath, various motion also exists in the head and limbs with each breath. Motion is to be considered in delivery of a proton dose to the body as the protons are preferentially delivered to the tumor and not to surrounding tissue. Motion thus results in an ambiguity in where the tumor resides relative to the beam path. To partially overcome this concern, protons are preferentially delivered at the same point in a breathing cycle.

Initially a rhythmic pattern of breathing of a subject is determined. The cycle is observed or measured. For example, a proton beam operator can observe when a subject is breathing or is between breaths and can time the delivery of the protons to a given period of each breath. Alternatively, the subject is told to inhale, exhale, and/or hold their breath and the protons are delivered during the commanded time period. Preferably, one or more sensors are used to determine the breathing cycle of the individual. For example, a breath monitoring sensor senses air flow by or through the mouth or nose. Another optional sensor is a chest motion sensor attached or affixed to a torso of the subject.

Once the rhythmic pattern of the subject's breathing is determined, a signal is optionally delivered to the subject to more precisely control the breathing frequency. For example, a display screen is placed in front of the subject directing the subject when to hold their breath and when to breathe. Typically, a breathing control module uses input from one or more of the breathing sensors. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor is positioned in front of the subject and the display monitor displays at least breathing commands to the subject. Typically, the subject is directed to hold their breath for a short period of time, such as about one-half, one, two, or three seconds. The period of time the subject is asked to hold their breath is less than about ten seconds as the period of time the breath is held is synchronized to the delivery time of the proton beam to the tumor, which is about one-half, one, two, or three seconds. While delivery of the protons at the bottom of the breath is preferred, protons are optionally delivered at any point in the breathing cycle, such as upon full inhalation. Delivery at the top of the breath or when the patient is directed to inhale deeply and hold their breath by the breathing control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the subject when they are about to be asked to hold their breath, such as with a 3, 2, 1, second countdown so that the subject is aware of the task they are about to be asked to perform.

A proton delivery control algorithm is used to synchronize delivery of the protons to the tumor within a given period of each breath, such as at the bottom of a breath when the subject is holding their breath. The proton delivery control algorithm is preferably integrated with the breathing control module. Thus, the proton delivery control algorithm knows when the subject is breathing, where in the breath cycle the subject is, and/or when the subject is holding their breath. The proton delivery control algorithm controls when protons are injected and/or inflected into the synchrotron, when an RF signal is applied to induce an oscillation, as described supra, and when a DC voltage is applied to extract protons from the synchrotron, as described supra. Typically, the proton delivery control algorithm initiates proton inflection and subsequent RF induced oscillation before the subject is directed to hold their breath or before the identified period of the breathing cycle selected for a proton delivery time. In this manner, the proton delivery control algorithm can deliver protons at a selected period of the breathing cycle by simultaneously or near simultaneously delivering the high DC voltage to the second pair of plates, described supra, that results in extraction of the protons from the synchrotron and subsequent delivery to the subject at the selected time point. Since the period of acceleration of protons in the synchrotron is constant, the proton delivery control algorithm is used to set an AC RF signal that matches the breathing cycle or directed breathing cycle of the subject.

Multi-Field Illumination

The 3-dimensional scanning system of the proton spot focal point, described supra, is preferably combined with a rotation/raster method. The method includes layer wise tumor irradiation from many directions. During a given irradiation slice, the proton beam energy is continuously changed according to the tissue's density in front of the tumor to result in the beam stopping point, defined by the Bragg peak, to always be inside the tumor and inside the irradiated slice. The novel method allows for irradiation from many directions, referred to herein as multi-field irradiation, to achieve the maximal effective dose at the tumor level while simultaneously significantly reducing possible side-effects on the surrounding healthy tissues in comparison with existing methods. Essentially, the multi-field irradiation system distributes dose-distribution at tissue depths not yet reaching the tumor.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:
1. An apparatus for tumor therapy using charged particles, the charged particles accelerated by a rounded corner polygon synchrotron, said synchrotron comprising:
a center; and
a charged particle circulation beam path running;
about said center;
through straight sections; and
through turning sections, wherein each of said turning sections comprise at least four bending magnets, said four bending magnets comprising at least eight edge focusing surfaces,
wherein said circulation beam path comprises a length of less than sixty meters, and
wherein a number of said straight sections equals a number of said turning sections.

2. The apparatus of claim 1, wherein said number of turning sections comprises exactly four turning sections, wherein each of said four turning sections turns the charged particle circulation beam path about ninety degrees, said synchrotron capable of accelerating the charged particles to at least 300 MeV.

3. The apparatus of claim 2, wherein said four turning sections comprise at least thirty-two charged particle edge focusing surfaces.

4. The apparatus of claim 1, wherein said turning sections comprise a total of exactly sixteen bending magnets, wherein said charged particle circulation beam path does not pass through any operational quadrupole magnets.

5. The apparatus of claim 1, each of said bending magnets comprising:
a gap, said charged particle beam path running through said gap, and
a core, wherein said core terminates at said gap with a surface comprising a finish of less than about ten microns polish.

6. The apparatus of claim 1, wherein said synchrotron further comprises:
an extraction material;
at least a one kilovolt direct current field applied across a pair of extraction blades; and
a deflector,
wherein the charged particles pass through said extraction material resulting in a reduced energy charged particle beam,
wherein the reduced energy charged particle beam passes between said pair of extraction blades, and
wherein the direct current field redirects the reduced energy charged particle beam through said deflector,
wherein said deflector yields an extracted charged particle beam.

7. The apparatus of claim 6, wherein said extraction material comprises a foil of about thirty to one hundred micrometers thickness,
wherein said extraction material comprises any of:
beryllium;
lithium hydride; and
carbon,
wherein said extraction material comprises atoms, said atoms consisting essentially of atoms having six or fewer protons.

8. The apparatus of claim 6, further comprising a pair of betatron oscillation inducing blades, wherein the charged particles traverse said pair of betatron oscillation inducing blades during acceleration.

9. The apparatus of claim 8, wherein a radio frequency voltage applied across said pair of betatron oscillation inducing blades induces a betatron oscillation on the circulating charged particles,
wherein the charged particles comprises a radius of curvature passing through said betatron oscillation inducing blades,
wherein the reduced energy charged particle beam, resulting from transmission through said extraction material, comprises a radius of curvature passing through said extraction blades, and
wherein a first distance between said center of said synchrotron and said pair of extraction blades is less than a second distance between said center of said synchrotron and said pair of betatron oscillation inducing blades.

10. The apparatus of claim 1, further comprising:
a first focusing edge; a second focusing edge; a third focusing edge; and a fourth focusing edge,
wherein said at least four bending magnets reside in a first of said turning sections,
wherein said at least four bending magnets comprise: a first bending magnet and a second bending magnet,
wherein said first bending magnet terminates on opposite sides with said first focusing edge and said second focusing edge,
wherein a first plane established by said first focusing edge intersects a plane established by said second focusing edge beyond said center of said synchrotron,
wherein said second bending magnet terminates on opposite sides with said third focusing edge and said fourth focusing edge,
wherein a second plane established by said third focusing edge intersects a plane established by said fourth focusing edge beyond said center of said synchrotron,
wherein all of said first focusing edge; said second focusing edge; said third focusing edge; and said fourth focusing edge bend the charged particles toward said center of said synchrotron.

11. The apparatus of claim 1, further comprising:
a winding coil, wherein a turn in said coil wraps around at least two of said turning magnets, wherein said turn does not occupy space directly between said at least two of said turning magnets.

12. A method for tumor therapy using charged particles, the charged particles accelerated by a rounded corner synchrotron, said method comprising the step of:
accelerating the charged particles in a charged particle circulation beam path running about a center of said synchrotron, said charged particle circulation beam path comprising:
straight sections; and
turning sections,
wherein said turning sections each comprise at least four bending magnets, said four bending magnets comprising at least eight surfaces having focusing geometry,
wherein said circulation beam path comprises a length of less than sixty meters, and
wherein a number of said straight sections equals a number of said turning sections.

13. The method of claim 12, further comprising the steps of:
accelerating the charged particles to at least 300 MeV using said synchrotron, wherein said number of turning sections comprises exactly four turning sections; and
turning the charged particles about ninety degrees with each of said four turning sections.

14. The method of claim 13, wherein said four turning sections comprise at least thirty-two charged particle edge focusing surfaces.

15. The method of claim 12, wherein said turning sections comprise at least twelve bending magnets, wherein said charged particle circulation beam path does not pass through any operational quadrupole magnets.

16. The method of claim 12, further comprising the step of:
running the charged particles through a gap, said gap running through each of said bending magnets, said gap comprising a surface finish of less than about ten microns polish, wherein each of said turning magnets comprises a core terminating at said gap.

17. The method of claim 12, further comprising the steps of:
transmitting the charged particles through an extraction material, said extraction material yielding a reduced energy charged particle beam;
applying at least five hundred volts across a first pair of blades; and
passing the reduced energy charged particle beam between said first pair of blades,
wherein said first pair of blades redirect the reduced energy charged particle beam to a deflector,
wherein said deflector yields an extracted charged particle beam.

18. The method of claim 17, wherein said extraction material comprises a foil of about forty to sixty microns thickness,
wherein said extraction material comprises any of:
beryllium;
lithium hydride; and
carbon, and
wherein said extraction material comprises atoms, said atoms consisting essentially of atoms having six or fewer protons.

19. The method of claim 12, further comprising the steps of:
transmitting the charged particles through an extraction material in said charged particle beam path, said extraction material yielding a reduced energy charged particle beam;
applying a field of at least five hundred volts across a pair of extraction blades, said charged particle beam path passing between said pair of extraction blades;
passing the reduced energy charged particle beam between said pair of extraction blades; and
prior to said step of transmitting, inducing betatron oscillation on the circulating charged particle beam,
wherein said field redirects the reduced energy charged particle as an extracted charged particle beam,
wherein said step of inducing occurs at a selected energy level of the circulating charged particle beam,
wherein the betatron oscillation increases average radius of curvature of the circulating charged particle beam until said step of transmitting yields the reduced energy charged particle beam,
wherein said step of inducing at said selected energy level yields an energy controlled extracted charged particle beam.

20. The method of claim 12, further comprising the step of:
bending the charged particles toward said center of said synchrotron using all of a first focusing edge, a second focusing edge, a third focusing edge, and a fourth focusing edge,
wherein said at least four bending magnets are located in a first of said turning sections,
wherein said at least four bending magnets comprise: a first bending magnet and a second bending magnet,
wherein said first bending magnet terminates on opposite sides with said first focusing edge and said second focusing edge,
wherein a first plane established by said first focusing edge intersects a plane established by said second focusing edge beyond said center of said synchrotron,
wherein said second bending magnet terminates on opposite sides with said third focusing edge and said fourth focusing edge, and
wherein a second plane established by said third focusing edge intersects a plane established by said fourth focusing edge beyond said center of said synchrotron.

21. The method of claim 20, wherein a first distance between said center of said synchrotron and said first pair of blades is less than a second distance between said center of said synchrotron and said second pair of blades,
wherein the circulating charged particle beam comprises a second radius of curvature passing through said second pair of blades,
wherein the reduced energy charged particle beam, resulting from transmission through said extraction material, comprises a first radius of curvature passing through said first pair of blades
wherein said reduced energy charged particle beam exits said synchrotron within an inner diameter of said circulating charged particle beam.

\* \* \* \* \*